(12) United States Patent
Phillips et al.

(10) Patent No.: US 9,577,197 B2
(45) Date of Patent: Feb. 21, 2017

(54) CONJUGATED POLYMERS

(75) Inventors: Amy Phillips, Hampshire (GB); Nicolas Blouin, Southampton (GB); William Mitchell, Chandler's Ford (GB); Steven Tierney, Southampton (GB)

(73) Assignee: MERCK PATENT GmbH, Darmstadt (DE)

( * ) Notice: Subject to any disclaimer, the term of this patent is extended or adjusted under 35 U.S.C. 154(b) by 209 days.

(21) Appl. No.: 14/234,235

(22) PCT Filed: Jun. 21, 2012

(86) PCT No.: PCT/EP2012/002626
§ 371 (c)(1),
(2), (4) Date: Mar. 12, 2014

(87) PCT Pub. No.: WO2013/010615
PCT Pub. Date: Jan. 24, 2013

(65) Prior Publication Data
US 2014/0175339 A1 Jun. 26, 2014

(30) Foreign Application Priority Data

Jul. 21, 2011 (EP) ..................................... 11005983

(51) Int. Cl.
*H01L 51/00* (2006.01)
*C07D 495/04* (2006.01)
*C08G 61/12* (2006.01)
*C07D 519/00* (2006.01)
*H01L 51/42* (2006.01)

(52) U.S. Cl.
CPC ......... *H01L 51/0036* (2013.01); *C07D 495/04* (2013.01); *C07D 519/00* (2013.01); *C08G 61/123* (2013.01); *C08G 61/126* (2013.01); *H01L 51/0043* (2013.01); *C08G 2261/3245* (2013.01); *C08G 2261/3246* (2013.01); *C08G 2261/3247* (2013.01); *H01L 51/4253* (2013.01); *Y02E 10/549* (2013.01)

(58) Field of Classification Search
CPC ... C07D 495/04; C07D 519/00; C08G 61/123; C08G 61/126; C08G 2261/3245; C08G 2261/3246; C08G 2261/3247; H01L 51/0036; H01L 51/0043; H01L 51/4253; Y02E 10/549
USPC .......... 252/511, 519.5, 519.4; 528/9; 549/43
See application file for complete search history.

(56) References Cited

U.S. PATENT DOCUMENTS

| 7,524,922 | B2 | 4/2009 | Heeney et al. |
| 8,304,512 | B2 | 11/2012 | Wigglesworth et al. |
| 8,367,798 | B2 | 2/2013 | Yang et al. |
| 2005/0082525 | A1 | 4/2005 | Heeney et al. |
| 2010/0078074 | A1 | 4/2010 | Yang et al. |
| 2011/0040069 | A1 | 2/2011 | Miura et al. |
| 2011/0178255 | A1 | 7/2011 | Wigglesworth et al. |
| 2015/0108409 | A1* | 4/2015 | Meyer .................. C07D 495/04 252/500 |

FOREIGN PATENT DOCUMENTS

| CA | 2727497 | A | 7/2011 |
| CN | 101945917 | A | 1/2011 |
| EP | 2248840 | A | 11/2010 |
| JP | 2005120379 | A | 5/2005 |
| JP | 2009215546 | A | 9/2009 |
| WO | 2011085004 | A | 7/2011 |

OTHER PUBLICATIONS

English Translation of Office Action for Related Chinese Patent Application No. 201280035415.1 issued Jan. 16, 2015.
Hassan, Z. et al., "Cyclization of 1,4-Phenylenediacrylic Acid with Thionyl Chloride and Subsequent Suzuki-Miyaura Reactions Revisited. The Products are Benzo[1,2-b;5,6-b']dithiophenes and not Benzo[1,2-b;4,5-b']dithiophenes," Adv. Synth. Catal., 2011.
International Search Report for PCT/EP2012/002626 dated Oct. 19, 2012.
Kumagai, J. et al., "Effect of the Substitution Pattern of Alkyl Side Chain in a Benzodithiophene Core pi-System on Intra and Inter-Molecular Charge Carrier Mobility," The Journal of Physical Chemistry B, 2011, vol. 115, pp. 8446-8452.
Office Action for Related Japanese Patent Application No. 2014-520546 dated Jun. 16, 2016.

* cited by examiner

*Primary Examiner* — Douglas McGinty
(74) *Attorney, Agent, or Firm* — Millen White Zelano and Branigan, PC; Csaba Henter; Anthony Zelano

(57) ABSTRACT

The invention relates to novel polymers containing one or more 3,7-dialkyl-benzo[1,2-b:4,5-b']dithiophene repeating units, methods for their preparation and monomers used therein, blends, mixtures and formulations containing them, the use of the polymers, blends, mixtures and formulations as semiconductor in organic electronic (OE) devices, especially in organic photovoltaic (OPV) devices, and to OE and OPV devices comprising these polymers, blends, mixtures or formulations.

19 Claims, No Drawings

CONJUGATED POLYMERS

FIELD OF THE INVENTION

The invention relates to novel polymers containing one or more 3,7-dialkyl-benzo[1,2-b:4,5-b']dithiophene repeating units, methods for their preparation and monomers used therein, blends, mixtures and formulations containing them, the use of the polymers, blends, mixtures and formulations as semiconductor in organic electronic (OE) devices, especially in organic photovoltaic (OPV) devices, and to OE and OPV devices comprising these polymers, blends, mixtures or formulations.

BACKGROUND OF THE INVENTION

In recent years there has been growing interest in the use of conjugated, semiconducting polymers for electronic applications. One particular area of importance is organic photovoltaics (OPV). Conjugated polymers have found use in OPVs as they allow devices to be manufactured by solution-processing techniques such as spin casting, dip coating or ink jet printing. Solution processing can be carried out cheaper and on a larger scale compared to the evaporative techniques used to make inorganic thin film devices. Currently, polymer based photovoltaic devices are achieving efficiencies up to 8%.

The conjugated polymer serves as the main absorber of the solar energy, therefore a low band gap is a basic requirement of the ideal polymer design to absorb the maximum of the solar spectrum. A commonly used strategy to provide conjugated polymers with narrow band gap is to utilize alternating copolymers consisting of both electron rich donor units and electron deficient acceptor units within the polymer backbone.

However, the conjugated polymers that have been suggested in prior art for use in OPV devices do still suffer from certain drawbacks. For example many polymers suffer from limited solubility in commonly used organic solvents, which can inhibit their suitability for device manufacturing methods based on solution processing, or show only limited power conversion efficiency in OPV bulk-hetero-junction devices, or have only limited charge carrier mobility, or are difficult to synthesize and require synthesis methods which are unsuitable for mass production.

Therefore, there is still a need for organic semiconducting (OSC) materials that are easy to synthesize, especially by methods suitable for mass production, show good structural organization and film-forming properties, exhibit good electronic properties, especially a high charge carrier mobility, good processibility, especially a high solubility in organic solvents, and high stability in air. Especially for use in OPV cells, there is a need for OSC materials having a low bandgap, which enable improved light harvesting by the photoactive layer and can lead to higher cell efficiencies, compared to the polymers from prior art.

It was an aim of the present invention to provide compounds for use as organic semiconducting materials that do not have the drawbacks of prior art materials as described above, are easy to synthesize, especially by methods suitable for mass production, and do especially show good processibility, high stability, good solubility in organic solvents, high charge carrier mobility, and a low bandgap. Another aim of the invention was to extend the pool of OSC materials available to the expert. Other aims of the present invention are immediately evident to the expert from the following detailed description.

The inventors of the present invention have found that one or more of the above aims can be achieved by providing conjugated copolymers containing a 3,7-disubstituted benzo[1,2-b:4,5-b']dithiophene (hereinafter shortly referred to as "BDT") repeating unit as donor and one or more heteroaryl units as acceptor.

It was found that these copolymers are attractive candidates for photovoltaic applications, specifically in bulk heterojunction (BHJ) photovoltaic devices. By the incorporation of the electron-donating BDT unit and an electron-accepting unit into a co-polymer i.e. a "donor-acceptor" polymer, a reduction of the bandgap can be achieved, which enables improved light harvesting properties in bulk heterojunction (BHJ) photovoltaic devices. Also, by modifying the BDT core unit with the addition of an alkyl functionality at the 3- and 7-positions, the solubility and electronic properties of the copolymer can be further optimised.

U.S. Pat. No. 7,524,922 B2 discloses polymers comprising a BDT unit that is substituted in 4- and 8-position and/or in 3- and 7-position by optionally substituted groups like alkyl or aryl groups.

US 2010/0078074 A1 discloses polymers comprising a BDT unit that is substituted in 4- and 8-position and/or in 3- and 7-position by a group selected from the group consisting of H, alkyl, alkoxy, cyano, nitro and optionally substituted aryl.

WO 2010/135701 A1 discloses polymers comprising a BDT unit that is substituted in 4- and 8-position and/or in 3- and 7-position by a group selected from broad variety including H, CN, alkoxy, thioalkyl, ketone, ester, sulfonate, alkyl, alkenyl, alkynyl, haloalkyl, cycloalkyl, aryl, haloaryl, cycloheteroalkyl and heteroaryl.

US 2011/049477 A1 discloses polymers comprising a BDT unit that is substituted in 4- and 8-position and/or in 3- and 7-position by a group selected from broad variety including H, alkyl, aryl, halogen, hydroxyl, aryloxy, alkoxy, alkenyl, alkynyl, amino, thioalkyl, phosphino, sily, —COR, COOK, —PO$_3$R$_2$, —OPO$_3$R$_2$ and CN.

US 2011/0040069 A1 discloses compounds and polymers comprising a polycyclic fused ring moiety, which consists of one to five fused benzene rings that are flanked on each side by one benzo-fused furan, thiophene or selenophene ring which is substituted by a halogen, alkyl or aryl group, and further discloses the use of these polymers in organic transistors.

However these documents do not disclose the specific copolymers as claimed in the present invention or their use in OPV devices.

SUMMARY OF THE INVENTION

The invention relates to conjugated polymers comprising, preferably consisting of, repeating units of formula I1 and repeating units of formula I2

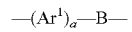    I1

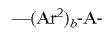    I2 wherein
B is a divalent group of the following formula

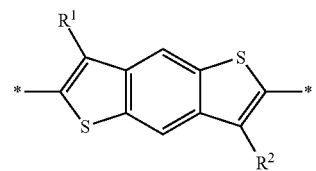

A is a divalent group of the following formula

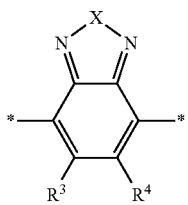

X is O, Se, Te, NR⁰ or S, $R^1$, $R^2$ denote independently of each other, and on each occurrence identically or differently, straight-chain, branched or cyclic alkyl with 1 to 30 C atoms, preferably with 1 to 20 C atoms, $R^3$, $R^4$ denote independently of each other, and on each occurrence identically or differently, H, F or straight-chain or branched alkyl or alkoxy with 1 to 30 C atoms, preferably with 1 to 20 C atoms, $Ar^1$, $Ar^2$ is, on each occurrence identically or differently, and independently of each other, aryl or heteroaryl that is different from B and A, preferably has 5 to 30 ring atoms, and is optionally substituted, preferably by one or more groups $R^S$, $R^S$ is on each occurrence identically or differently F, Br, Cl, —CN, —NC, —NCO, —NCS, —OCN, —SCN, —C(O)NR⁰R⁰⁰, —C(O)X⁰, —C(O)R⁰, —NH₂, —NR⁰R⁰⁰, —SH, —SR⁰, —SO₃H, —SO₂R⁰, —OH, —NO₂, —CF₃, —SF₅, optionally substituted silyl, carbyl or hydrocarbyl with 1 to 40 C atoms that is optionally substituted and optionally comprises one or more hetero atoms, R⁰, R⁰⁰ are independently of each other H or optionally substituted $C_{1-40}$ carbyl or hydrocarbyl, X⁰ is halogen, preferably F, Cl or Br, a, b are independently of each other 1, 2 or 3.

In the polymers of the present invention, groups A and B are not directly linked to each other (i.e. there are no couplings A-A, B-B, A-B or B-A).

The invention further relates to the use of these conjugated polymers as p-type semiconductor, preferably as electron donor component in semiconducting materials, formulations, blends, devices or components of devices.

The invention further relates to a semiconducting material, formulation, blend, device or component of a device comprising a conjugated polymer as described above and below as electron donor component, and preferably further comprising one or more compounds or polymers having electron acceptor properties.

The invention further relates to a mixture or blend comprising one or more conjugated polymers as described above and below and one or more additional compounds or polymers which are preferably selected from compounds and polymers having one or more of semiconducting, charge transport, hole or electron transport, hole or electron blocking, electrically conducting, photoconducting or light emitting properties.

The invention further relates to a mixture or blend as described above and below, which comprises one or more conjugated polymers as described above and below, and one or more n-type organic semiconductor compounds, preferably selected from fullerenes or substituted fullerenes.

The invention further relates to a formulation comprising one or more polymers, mixtures or blends as described above and below and optionally one or more solvents, preferably selected from organic solvents.

The invention further relates to the use of polymers, mixtures, blends and formulations according to the present invention as charge transport, semiconducting, electrically conducting, photoconducting or light emitting material in optical, electrooptical, electronic, electroluminescent or photoluminescent components or devices.

The invention further relates to a charge transport, semiconducting, electrically conducting, photoconducting or light emitting material or component comprising one or more polymers, polymer blends of formulations according to the present invention.

The invention further relates to an optical, electrooptical or electronic component or device comprising one or more polymers, polymer blends, formulations, components or materials according to the present invention.

The optical, electrooptical, electronic electroluminescent and photoluminescent components or devices include, without limitation, organic field effect transistors (OFET), thin film transistors (TFT), integrated circuits (IC), logic circuits, capacitors, radio frequency identification (RFID) tags, devices or components, organic light emitting diodes (OLED), organic light emitting transistors (OLET), flat panel displays, backlights of displays, organic photovoltaic devices (OPV), solar cells, laser diodes, photoconductors, photodetectors, electrophotographic devices, electrophotographic recording devices, organic memory devices, sensor devices, charge injection layers, charge transport layers or interlayers in polymer light emitting diodes (PLEDs), organic plasmon-emitting diodes (OPEDs), Schottky diodes, planarising layers, antistatic films, polymer electrolyte membranes (PEM), conducting substrates, conducting patterns, electrode materials in batteries, alignment layers, biosensors, biochips, security markings, security devices, and components or devices for detecting and discriminating DNA sequences.

DETAILED DESCRIPTION OF THE INVENTION

The monomers and polymers of the present invention are easy to synthesize and exhibit advantageous properties. The conjugated polymers of the present invention show good processability for the device manufacture process, high solubility in organic solvents, and are especially suitable for large scale production using solution processing methods. At the same time, they show a low bandgap, high charge carrier mobility, high external quantum efficiency in BHJ solar cells, good morphology when used in p/n-type blends e.g. with fullerenes, high oxidative stability, and a long lifetime in electronic devices, and are promising materials for organic electronic OE devices, especially for OPV devices with high power conversion efficiency.

The polymers of the present invention are especially suitable for the preparation of blends of p-type and n-type semiconductors which are useful for application in bulk heterojunction photovoltaic devices.

In addition, they show the following advantageous properties:

i) Compared to 4,8-disubstituted-benzo[1,2-b:4,5-b']dithiophene, the 3,7-disubstituted-benzo[1,2-b:4,5-b']dithiophene core leads to alternative solubility and morphology profile. Such difference has impact on the OPV device fabrication process and performance.

ii) Compared to polymers based on 4,8-disubstituted-benzo[1,2-b:4,5-b']dithiophene, the polymers based on 3,7-disubstituted-benzo[1,2-b:4,5-b']dithiophene exhibit higher open circuit voltage $V_{oc}$.

The synthesis of the polymers and the monomers of the present invention can be achieved based on methods that are known to the skilled person and described in the literature, as will be further illustrated herein.

Above and below, the term "polymer" generally means a molecule of high relative molecular mass, the structure of which essentially comprises the multiple repetition of units derived, actually or conceptually, from molecules of low relative molecular mass (PAC, 1996, 68, 2291). The term "oligomer" generally means a molecule of intermediate relative molecular mass, the structure of which essentially comprises a small plurality of units derived, actually or conceptually, from molecules of lower relative molecular mass (PAC, 1996, 68, 2291). In a preferred sense according to the present invention a polymer means a compound having >1, i.e. at least 2 repeating units, preferably ≥5 repeating units, and an oligomer means a compound with >1 and <10, preferably <5, repeating units.

Above and below, in a formula showing a polymer or a repeating unit, an asterisk ("*") denotes a linkage to an adjacent repeating unit or a terminal group in the polymer chain.

The terms "repeating unit" and "monomeric unit" mean the constitutional repeating unit (CRU), which is the smallest constitutional unit the repetition of which constitutes a regular macromolecule, a regular oligomer molecule, a regular block or a regular chain (PAC, 1996, 68, 2291).

The terms "donor" and "acceptor", unless stated otherwise, mean an electron donor or electron acceptor, respectively. "Electron donor" means a chemical entity that donates electrons to another compound or another group of atoms of a compound. "Electron acceptor" means a chemical entity that accepts electrons transferred to it from another compound or another group of atoms of a compound. (see also U.S. Environmental Protection Agency, 2009, Glossary of technical terms, http://www.epa.gov/oust/cat/TUM-GLOSS.HTM).

The term "leaving group" means an atom or group (charged or uncharged) that becomes detached from an atom in what is considered to be the residual or main part of the molecule taking part in a specified reaction (see also PAC, 1994, 66, 1134).

The term "conjugated" means a compound containing mainly C atoms with $sp^2$-hybridisation (or optionally also sp-hybridisation), which may also be replaced by hetero atoms. In the simplest case this is for example a compound with alternating C—C single and double (or triple) bonds, but does also include compounds with units like 1,3-phenylene. "Mainly" means in this connection that a compound with naturally (spontaneously) occurring defects, which may lead to interruption of the conjugation, is still regarded as a conjugated compound.

Unless stated otherwise, the molecular weight is given as the number average molecular weight $M_n$ or weight average molecular weight $M_w$, which is determined by gel permeation chromatography (GPC) against polystyrene standards in eluent solvents such as tetrahydrofuran, trichloromethane (TCM, chloroform), chlorobenzene or 1,2,4-trichlorobenzene. Unless stated otherwise, 1,2,4-trichlorobenzene is used as solvent. The degree of polymerization, also referred to as total number of repeating units, n, means the number average degree of polymerization given as $n=M_n/M_U$, wherein $M_n$ is the number average molecular weight and $M_U$ is the molecular weight of the single repeating unit, see J. M. G. Cowie, *Polymers: Chemistry & Physics of Modern Materials*, Blackie, Glasgow, 1991.

The term "carbyl group" as used above and below denotes any monovalent or multivalent organic radical moiety which comprises at least one carbon atom either without any non-carbon atoms (like for example —C≡C—), or optionally combined with at least one non-carbon atom such as N, O, S, P, Si, Se, As, Te or Ge (for example carbonyl etc.). The term "hydrocarbyl group" denotes a carbyl group that does additionally contain one or more H atoms and optionally contains one or more hetero atoms like for example N, O, S, P, Si, Se, As, Te or Ge.

The term "hetero atom" means an atom in an organic compound that is not a H- or C-atom, and preferably means N, O, S, P, Si, Se, As, Te or Ge.

A carbyl or hydrocarbyl group comprising a chain of 3 or more C atoms may be straight-chain, branched and/or cyclic, including spiro and/or fused rings.

Preferred carbyl and hydrocarbyl groups include alkyl, alkoxy, alkylcarbonyl, alkoxycarbonyl, alkylcarbonyloxy and alkoxycarbonyloxy, each of which is optionally substituted and has 1 to 40, preferably 1 to 25, very preferably 1 to 18 C atoms, furthermore optionally substituted aryl or aryloxy having 6 to 40, preferably 6 to 25 C atoms, furthermore alkylaryloxy, arylcarbonyl, aryloxycarbonyl, arylcarbonyloxy and aryloxycarbonyloxy, each of which is optionally substituted and has 6 to 40, preferably 7 to 40 C atoms, wherein all these groups do optionally contain one or more hetero atoms, preferably selected from N, O, S, P, Si, Se, As, Te and Ge.

The carbyl or hydrocarbyl group may be a saturated or unsaturated acyclic group, or a saturated or unsaturated cyclic group. Unsaturated acyclic or cyclic groups are preferred, especially aryl, alkenyl and alkynyl groups (especially ethynyl). Where the $C_1$-$C_{40}$ carbyl or hydrocarbyl group is acyclic, the group may be straight-chain or branched. The $C_1$-$C_{40}$ carbyl or hydrocarbyl group includes for example: a $C_1$-$C_{40}$ alkyl group, a $C_1$-$C_{40}$ alkoxy or oxaalkyl group, a $C_2$-$C_{40}$ alkenyl group, a $C_2$-$C_{40}$ alkynyl group, a $C_3$-$C_{40}$ alkyl group, a $C_4$-$C_{40}$ alkyldienyl group, a $C_4$-$C_{40}$ polyenyl group, a $C_6$-$C_{18}$ aryl group, a $C_6$-$C_{40}$ alkylaryl group, a $C_6$-$C_{40}$ arylalkyl group, a $C_4$-$C_{40}$ cycloalkyl group, a $C_4$-$C_{40}$ cycloalkenyl group, and the like. Preferred among the foregoing groups are a $C_1$-$C_{20}$ alkyl group, a $C_2$-$C_{20}$ alkenyl group, a $C_2$-$C_{20}$ alkynyl group, a $C_3$-$C_{20}$ alkyl group, a $C_4$-$C_{20}$ alkyldienyl group, a $C_6$-$C_{12}$ aryl group, and a $C_4$-$C_{20}$ polyenyl group, respectively. Also included are combinations of groups having carbon atoms and groups having hetero atoms, like e.g. an alkynyl group, preferably ethynyl, that is substituted with a silyl group, preferably a trialkylsilyl group.

Aryl and heteroaryl preferably denote a mono-, bi- or tricyclic aromatic or heteroaromatic group with 4 to 30 ring C atoms that may also comprise condensed rings and is optionally substituted with one or more groups L, wherein L is selected from halogen, —CN, —NC, —NCO, —NCS, —OCN, —SCN, —C(=O)NR$^0$R$^{00}$, —C(=O)X, —C(=O)R$^0$, —NH$_2$, —NR$^0$R$^{00}$, —SH, —SR$^0$, —SO$_3$H, —SO$_2$R$^0$, —OH, —NO$_2$, —CF$_3$, —SF$_5$, P-Sp-, optionally substituted silyl, or carbyl or hydrocarbyl with 1 to 40 C atoms that is optionally substituted and optionally comprises one or more hetero atoms, and is preferably alkyl, alkoxy, thiaalkyl, alkylcarbonyl, alkoxycarbonyl or alkoxycarbonyloxy with 1 to 20 C atoms that is optionally fluorinated, and R$^0$, R$^{00}$, X$^0$, P and Sp have the meanings given above and below.

Very preferred substituents L are selected from halogen, most preferably F, or alkyl, alkoxy, oxaalkyl, thioalkyl, fluoroalkyl and fluoroalkoxy with 1 to 12 C atoms or alkenyl, alkynyl with 2 to 12 C atoms.

Especially preferred aryl and heteroaryl groups are phenyl in which, in addition, one or more CH groups may be replaced by N, naphthalene, thiophene, selenophene, thienothiophene, dithienothiophene, fluorene and oxazole, all of which can be unsubstituted, mono- or polysubstituted with L as defined above. Very preferred rings are selected from pyrrole, preferably N-pyrrole, furan, pyridine, preferably 2- or 3-pyridine, pyrimidine, pyridazine, pyrazine, triazole, tetrazole, pyrazole, imidazole, isothiazole, thiazole, thiadiazole, isoxazole, oxazole, oxadiazole, thiophene preferably 2-thiophene, selenophene, preferably 2-selenophene, thieno[3,2-b]thiophene, indole, isoindole, benzofuran, benzothiophene, benzodithiophene, quinole, 2-methylquinole, isoquinole, quinoxaline, quinazoline, benzotriazole, benzimidazole, benzothiazole, benzisothiazole, benzisoxazole, benzoxadiazole, benzoxazole, benzothiadiazole, all of which can be unsubstituted, mono- or polysubstituted with L as defined above. Further examples of heteroaryl groups are those selected from the following formulae An alkyl or alkoxy radical, i.e. where the terminal $CH_2$ group is replaced by —O—, can be straight-chain or branched. It is preferably straight-chain, has 2, 3, 4, 5, 6, 7 or 8 carbon atoms and accordingly is preferably ethyl, propyl, butyl, pentyl, hexyl, heptyl, octyl, ethoxy, propoxy, butoxy, pentoxy, hexoxy, heptoxy, or octoxy, furthermore methyl, nonyl, decyl, undecyl, dodecyl, tridecyl, tetradecyl, pentadecyl, nonoxy, decoxy, undecoxy, dodecoxy, tridecoxy or tetradecoxy, for example.

An alkenyl group, wherein one or more $CH_2$ groups are replaced by —CH=CH— can be straight-chain or branched. It is preferably straight-chain, has 2 to 10 C atoms and accordingly is preferably vinyl, prop-1-, or prop-2-enyl, but-1-, 2- or but-3-enyl, pent-1-, 2-, 3- or pent-4-enyl, hex-1-, 2-, 3-, 4- or hex-5-enyl, hept-1-, 2-, 3-, 4-, 5- or hept-6-enyl, oct-1-, 2-, 3-, 4-, 5-, 6- or oct-7-enyl, non-1-, 2-, 3-, 4-, 5-, 6-, 7- or non-8-enyl, dec-1-, 2-, 3-, 4-, 5-, 6-, 7-, 8- or dec-9-enyl.

Especially preferred alkenyl groups are $C_2$-$C_7$-1E-alkenyl, $C_4$-$C_7$-3E-alkenyl, $C_5$-$C_7$-4-alkenyl, $C_6$-$C_7$-5-alkenyl and $C_7$-6-alkenyl, in particular $C_2$-$C_7$-1E-alkenyl, $C_4$-$C_7$-3E-alkenyl and $C_5$-$C_7$-4-alkenyl. Examples for particularly preferred alkenyl groups are vinyl, 1E-propenyl, 1E-butenyl, 1E-pentenyl, 1E-hexenyl, 1E-heptenyl, 3-butenyl, 3E-pentenyl, 3E-hexenyl, 3E-heptenyl, 4-pentenyl, 4Z-hexenyl, 4E-hexenyl, 4Z-heptenyl, 5-hexenyl, 6-heptenyl and the like. Groups having up to 5 C atoms are generally preferred.

An oxaalkyl group, i.e. where one $CH_2$ group is replaced by —O—, is preferably straight-chain 2-oxapropyl (=methoxymethyl), 2-(=ethoxymethyl) or 3-oxabutyl (=2-methoxyethyl), 2-, 3-, or 4-oxapentyl, 2-, 3-, 4-, or 5-oxahexyl, 2-, 3-, 4-, 5-, or 6-oxaheptyl, 2-, 3-, 4-, 5-, 6- or 7-oxaoctyl, 2-, 3-, 4-, 5-, 6-, 7- or 8-oxanonyl or 2-, 3-, 4-, 5-, 6-, 7-, 8- or 9-oxadecyl, for example. Oxaalkyl, i.e. where one $CH_2$ group is replaced by —O—, is preferably straight-chain 2-oxapropyl (=methoxymethyl), 2-(=ethoxymethyl) or 3-oxabutyl (=2-methoxyethyl), 2-, 3-, or 4-oxapentyl, 2-, 3-, 4-, or 5-oxahexyl, 2-, 3-, 4-, 5-, or 6-oxaheptyl, 2-, 3-, 4-, 5-, 6- or 7-oxaoctyl, 2-, 3-, 4-, 5-, 6-, 7- or 8-oxanonyl or 2-, 3-, 4-, 5-, 6-, 7-, 8- or 9-oxadecyl, for example.

In an alkyl group wherein one $CH_2$ group is replaced by —O— and one by —C(O)—, these radicals are preferably neighboured. Accordingly these radicals together form a carbonyloxy group —C(O)—O— or an oxycarbonyl group —O—C(O)—. Preferably this group is straight-chain and has 2 to 6 C atoms. It is accordingly preferably acetyloxy, propionyloxy, butyryloxy, pentanoyloxy, hexanoyloxy, acetyloxymethyl, propionyloxymethyl, butyryloxymethyl, pentanoyloxymethyl, 2-acetyloxyethyl, 2-propionyloxyethyl, 2-butyryloxyethyl, 3-acetyloxypropyl, 3-propionyloxypropyl, 4-acetyloxybutyl, methoxycarbonyl, ethoxycarbonyl, propoxycarbonyl, butoxycarbonyl, pentoxycarbonyl, methoxycarbonylmethyl, ethoxy-carbonylmethyl, propoxy-carbonylmethyl, butoxycarbonylmethyl, 2-(methoxycarbonyl)ethyl, 2-(ethoxycarbonyl)ethyl, 2-(propoxy-carbonyl)ethyl, 3-(methoxycarbonyl)propyl, 3-(ethoxycarbonyl)propyl, 4-(methoxycarbonyl)-butyl.

An alkyl group wherein two or more $CH_2$ groups are replaced by —O— and/or —C(O)O— can be straight-chain or branched. It is preferably straight-chain and has 3 to 12 C atoms. Accordingly it is preferably bis-carboxy-methyl, 2,2-bis-carboxy-ethyl, 3,3-bis-carboxy-propyl, 4,4-bis-carboxy-butyl, 5,5-bis-carboxy-pentyl, 6,6-bis-carboxy-hexyl, 7,7-bis-carboxy-heptyl, 8,8-bis-carboxy-octyl, 9,9-bis-carboxy-nonyl, 10,10-bis-carboxy-decyl, bis-(methoxycarbonyl)-methyl, 2,2-bis-(methoxycarbonyl)-ethyl, 3,3-bis-(methoxycarbonyl)-propyl, 4,4-bis-(methoxycarbonyl)-butyl, 5,5-bis-(methoxycarbonyl)-pentyl, 6,6-bis-(methoxycarbonyl)-hexyl, 7,7-bis-(methoxycarbonyl)-heptyl, 8,8-bis-(methoxycarbonyl)-octyl, bis-(ethoxycarbonyl)-methyl, 2,2-bis-(ethoxycarbonyl)-ethyl, 3,3-bis-(ethoxycarbonyl)-propyl, 4,4-bis-(ethoxycarbonyl)-butyl, 5,5-bis-(ethoxycarbonyl)-hexyl.

A thioalkyl group, i.e where one $CH_2$ group is replaced by —S—, is preferably straight-chain thiomethyl (—$SCH_3$), 1-thioethyl (—$SCH_2CH_3$), 1-thiopropyl (=—$SCH_2CH_2CH_3$), 1-(thiobutyl), 1-(thiopentyl), 1-(thiohexyl), 1-(thioheptyl), 1-(thiooctyl), 1-(thiononyl), 1-(thiodecyl), 1-(thioundecyl) or 1-(thiododecyl), wherein preferably the $CH_2$ group adjacent to the $sp^2$ hybridised vinyl carbon atom is replaced.

A fluoroalkyl group is preferably straight-chain perfluoroalkyl $C_iF_{2i+1}$, wherein i is an integer from 1 to 15, in particular $CF_3$, $O_2F_5$, $C_3F_7$, $C_4F_9$, $C_5F_{11}$, $C_6F_{13}$, $C_7F_{15}$ or $CO_8F_{17}$, very preferably $C_6F_{13}$.

The above-mentioned alkyl, alkoxy, alkenyl, oxaalkyl, thioalkyl, carbonyl and carbonyloxy groups can be achiral or chiral groups. Particularly preferred chiral groups are 2-butyl (=1-methylpropyl), 2-methylbutyl, 2-methylpentyl, 3-methylpentyl, 2-ethylhexyl, 2-propylpentyl, in particular 2-methylbutyl, 2-methylbutoxy, 2-methylpentoxy, 3-methylpentoxy, 2-ethyl-hexoxy, 1-methylhexoxy, 2-octyloxy, 2-oxa-3-methylbutyl, 3-oxa-4-methyl-pentyl, 4-methylhexyl, 2-hexyl, 2-octyl, 2-nonyl, 2-decyl, 2-dodecyl, 6-meth-oxyoctoxy, 6-methyloctoxy, 6-methyloctanoyloxy, 5-methylheptyloxy-carbonyl, 2-methylbutyryloxy, 3-methylvaleroyloxy, 4-methylhexanoyloxy, 2-chloropropionyloxy, 2-chloro-3-methylbutyryloxy, 2-chloro-4-methyl-valeryl-oxy, 2-chloro-3-methylvaleryloxy, 2-methyl-3-oxapentyl, 2-methyl-3-oxahexyl, 1-methoxypropyl-2-oxy, 1-ethoxypropyl-2-oxy, 1-propoxypropyl-2-oxy, 1-butoxypropyl-2-oxy, 2-fluorooctyloxy, 2-fluorodecyloxy, 1,1,1-trifluoro-2-octyloxy, 1,1,1-trifluoro-2-octyl, 2-fluoromethyloctyloxy for example. Very preferred are 2-hexyl, 2-octyl, 2-octyloxy, 1,1,1-trifluoro-2-hexyl, 1,1,1-trifluoro-2-octyl and 1,1,1-trifluoro-2-octyloxy.

Preferred achiral branched groups are isopropyl, isobutyl (=methylpropyl), isopentyl (=3-methylbutyl), tert. butyl, isopropoxy, 2-methyl-propoxy and 3-methylbutoxy.

In another preferred embodiment of the present invention, $R^{1-4}$ are independently of each other selected from primary, secondary or tertiary alkyl or alkoxy with 1 to 30 C atoms, wherein one or more H atoms are optionally replaced by F, or aryl, aryloxy, heteroaryl or heteroaryloxy that is optionally alkylated or alkoxylated and has 4 to 30 ring atoms.

Very preferred groups of this type are selected from the group consisting of the following formulae

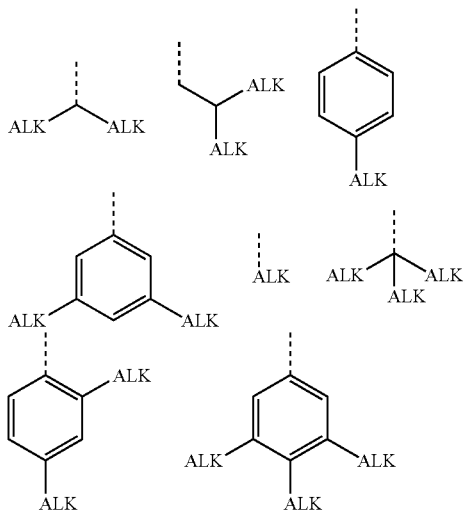

wherein "ALK" denotes optionally fluorinated, preferably linear, alkyl or alkoxy with 1 to 20, preferably 1 to 12 C-atoms, in case of tertiary groups very preferably 1 to 9 C atoms, and the dashed line denotes the link to the ring to which these groups are attached. Especially preferred among these groups are those wherein all ALK subgroups are identical.

—CY$^1$=CY$^2$— is preferably —CH=CH—, —CF=CF— or —CH=C(CN)—.

Halogen is F, Cl, Br or I, preferably F, Cl or Br.

—CO—, —C(=O)— and —C(O)— denote a carbonyl group, i.e.

The conjugated polymers according to the present invention are preferably selected of formula II:

—([(Ar$^1$)$_a$—B]$_x$—[(Ar$^2$)$_b$-A]$_y$)$_n$—,  II wherein A, B, Ar$^1$, Ar$^2$, a and b are as defined in formula I1 and I2,
x is the mole fraction of units (Ar$^1$)$_a$—B and is >0 and <1,
y is the mole fraction of units (Ar$^2$)$_b$-A and is >0 and <1,
x+y is 1,
n is an integer >1.

Preferred polymers of formula II are selected of the following formulae

\*—[Ar$^1$—B—Ar$^2$-A]$_n$—\*  II1

\*—[(Ar$^1$—B)$_x$—(Ar$^2$-A)$_y$]$_n$—\*  II2 wherein A, B, Ar$^1$, Ar$^2$, x, y and n are as defined in formula II.

In the polymers according to the present invention, the total number of repeating units n is preferably from 2 to 10,000. The total number of repeating units n is preferably ≥5, very preferably ≥10, most preferably ≥50, and preferably ≤500, very preferably ≤1,000, most preferably ≤2,000, including any combination of the aforementioned lower and upper limits of n.

The polymers of the present invention include alternating copolymers, random copolymers, block copolymers, and combinations thereof.

Further preferred polymers are selected of formula III

R$^5$-chain-R$^6$  III wherein "chain" denotes a polymer chain of formulae II, II1 or II2, and R$^5$ and R$^6$ have independently of each other one of the meanings of R$^1$ as defined above, and preferably denote, independently of each other, H, F, Br, Cl, —CH$_2$Cl, —CHO, —CH=CH$_2$, —SiR'R"R'", —SnR'R"R'", —BR'R", —B(OR')(OR"), —B(OH)$_2$, —C≡CH, —C≡CSiR$_{13}$, —ZnX or an endcap group, X is halogen, and R', R" and R'" have independently of each other one of the meanings of R$^0$ given in formula I, and two of R', R" and R'" may also form a ring together with the hetero atom to which they are attached In the polymers of formula II, II1 and II2, x denotes the mole fraction of units (Ar$^1$)$_a$—B, y denotes the mole fraction of units (Ar$^2$)$_b$-A, and n denotes the degree of polymerisation or total number of repeating. These formulae includes block copolymers, random copolymers and alternating copolymers formed by units (Ar$^1$)$_a$—B and (Ar$^2$)$_b$-A.

Another aspect of the invention relates to monomers of formula IV

R$^5$—(Ar$^1$)$_c$—B—(Ar$^2$)$_d$—R$^6$  IV wherein B, Ar$^1$, Ar$^2$ are as defined in formula I1, R$^5$ and R$^6$ are as defined in formula III, and c and d are independently of each other 0, 1, 2 or 3, wherein at least one of R$^5$ and R$^6$, preferably both R$^5$ and R$^6$, are different from H.

Especially preferred are monomers of the following formulae

R$^5$—Ar$^1$—B—Ar$^2$—R$^6$  IV1

R$^5$—B—R$^6$  IV2

R$^5$—Ar$^1$—B—R$^6$  IV3

R$^5$—B—Ar$^2$—R$^6$  IV4 wherein B, Ar$^1$, Ar$^2$, R$^5$ and R$^6$ are as defined in formula IV.

Especially preferred are monomers of formula IV and IV1-IV4 wherein R$^5$ and R$^6$ are, preferably independently of each other, selected from the group consisting of Cl, Br, I, O-tosylate, O-triflate, O-mesylate, O-nonaflate, —SiMe$_2$F, —SiMeF$_2$, —O—SO$_2$Z$^1$, —B(OZ$^2$)$_2$, —CZ$^3$=C(Z$^3$)$_2$, —C≡CH, —C≡CSi(Z)$_3$, —ZnX$^0$ and —Sn(Z$^4$)$_3$, wherein X$^0$ is halogen, Z$^{1-4}$ are selected from the group consisting of alkyl and aryl, each being optionally substituted, and two groups Z$^2$ may also form a cyclic group.

Very preferred are monomers and polymers of the present invention wherein Ar$^1$ and Ar$^2$ are selected from the group consisting of the following formulae

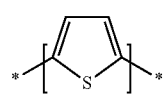

I1

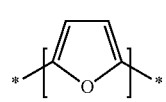

I2

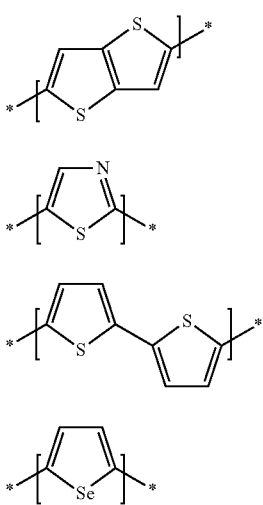
wherein the heterocyclic rings are optionally substituted by one or two groups R¹ or R³ as defined in formula I.
Further preferred are monomers and polymers of the present invention wherein one or more of Ar¹ and Ar² denote aryl or heteroaryl, preferably having electron donor properties, selected from the group consisting of the following formulae
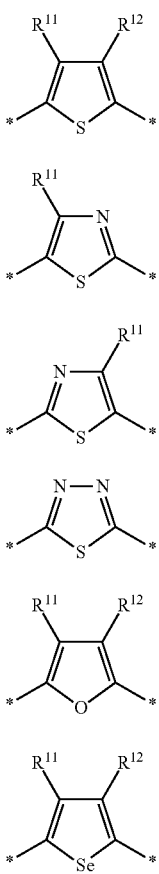
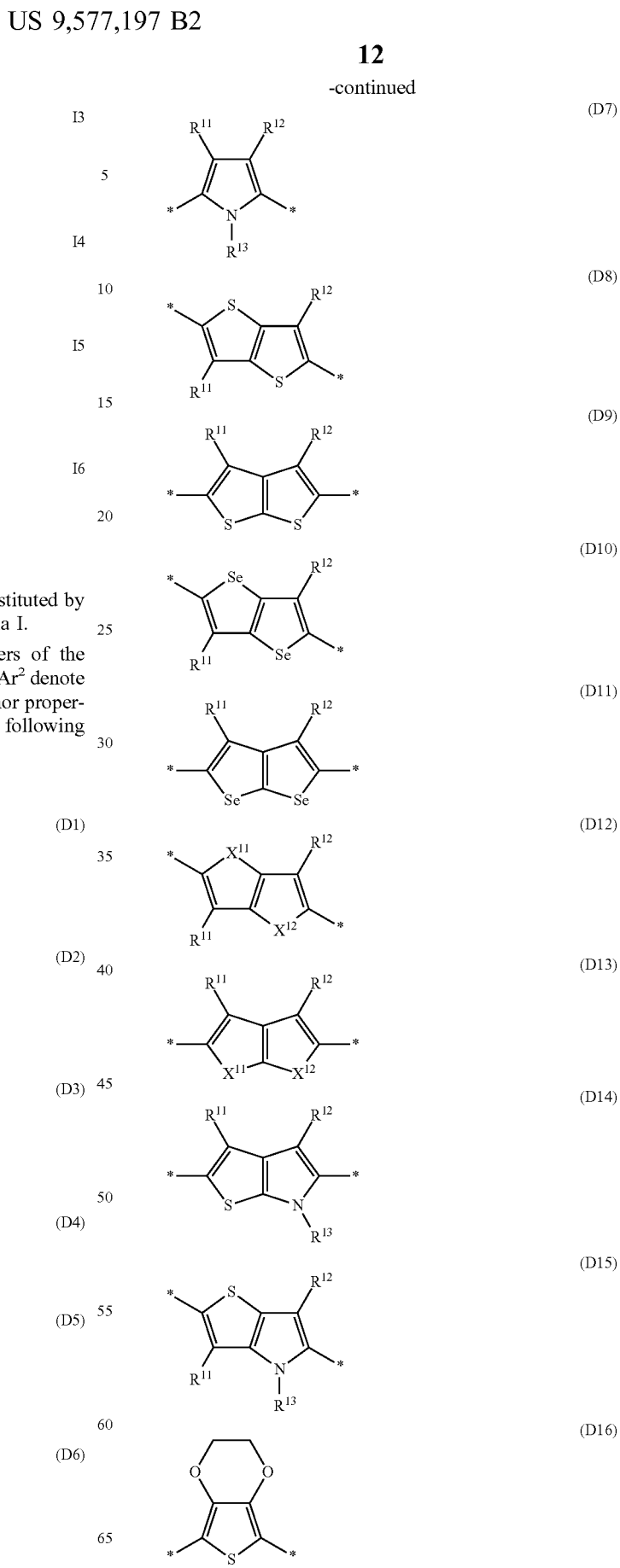

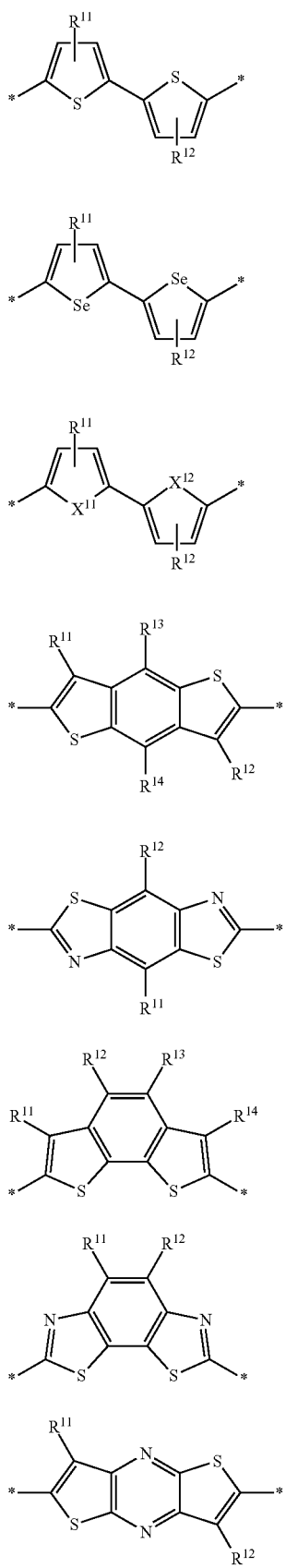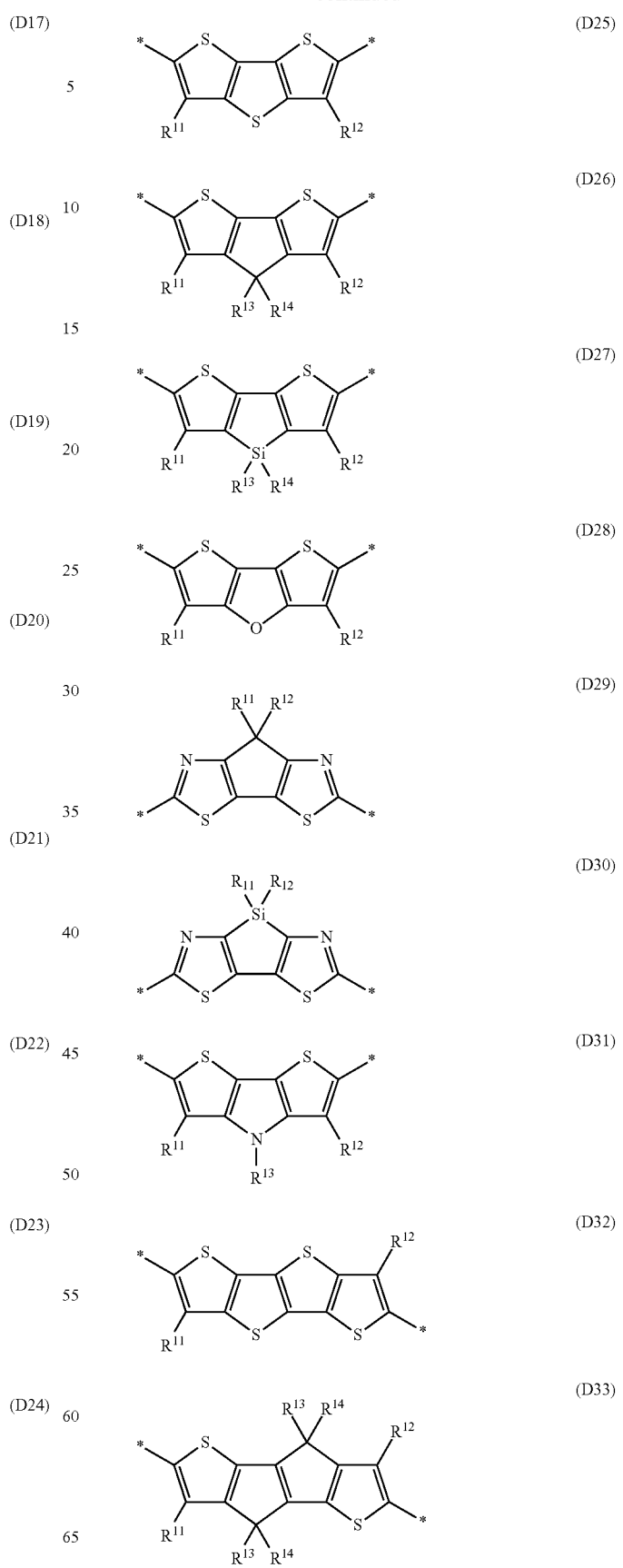

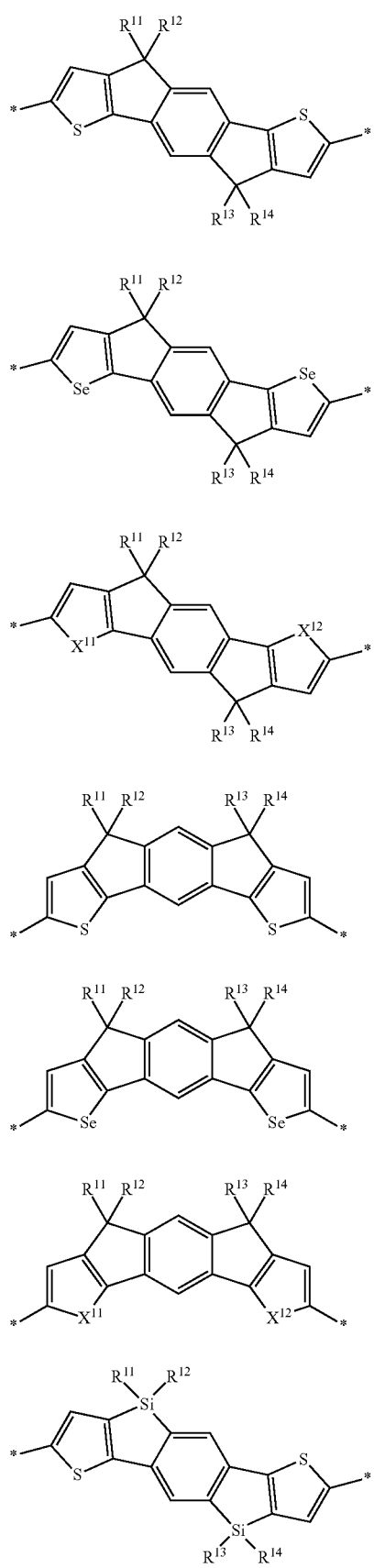
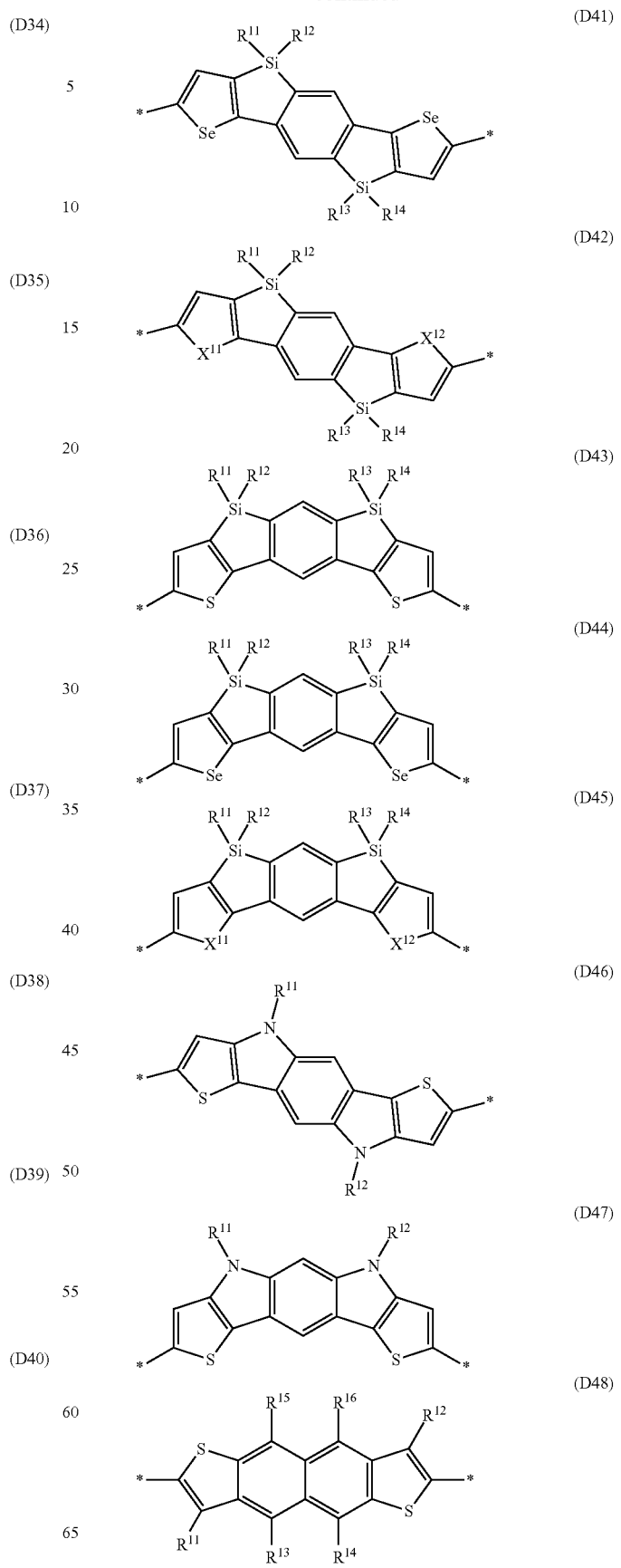

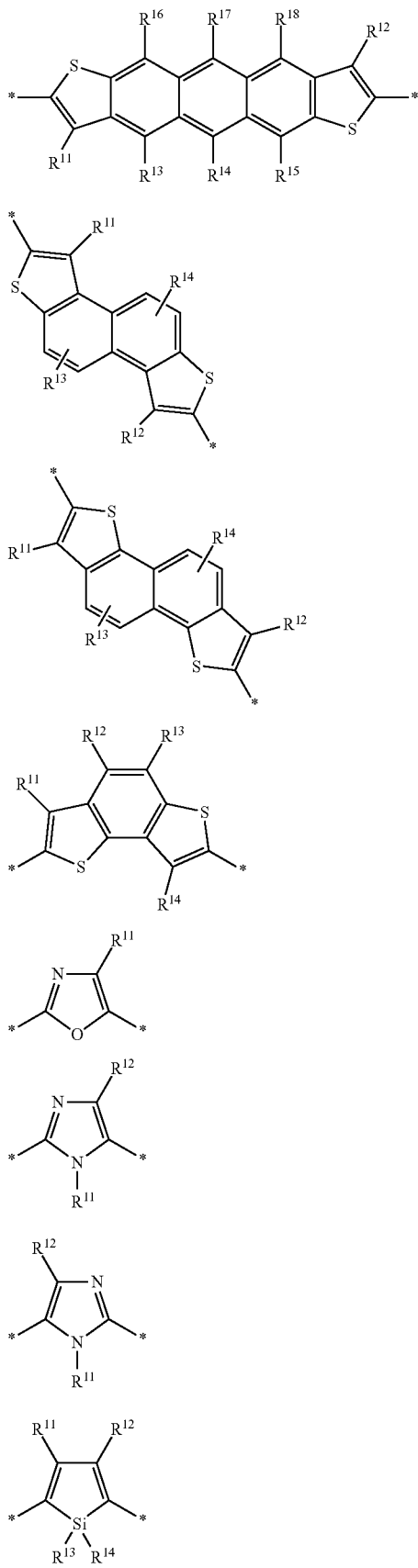
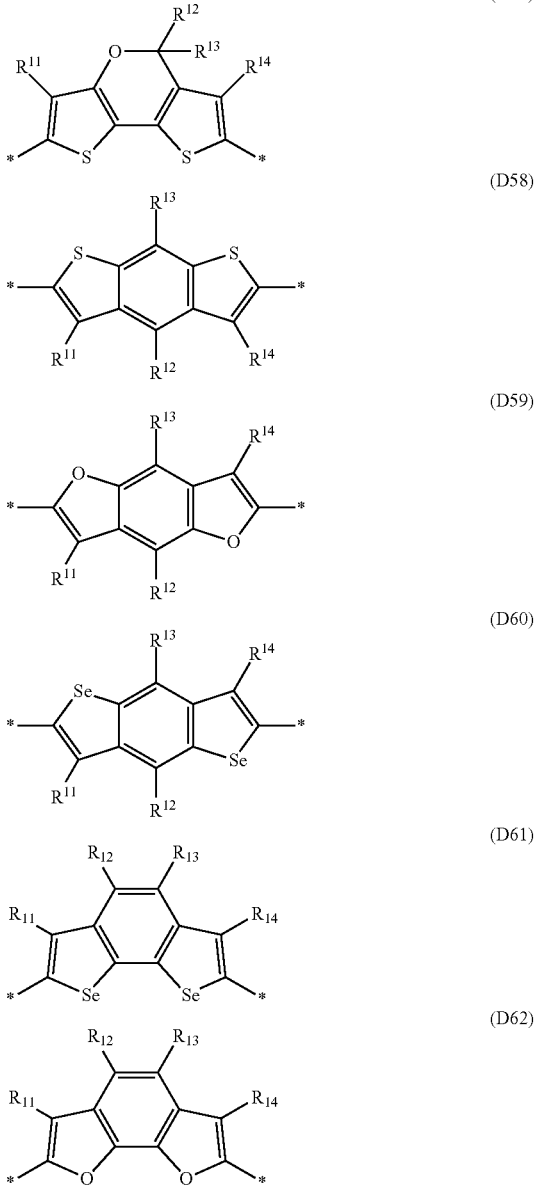

wherein one of $X^{11}$ and $X^{12}$ is S and the other is Se, and $R^{11}$, $R^{12}$, $R^{13}$, $R^{14}$, $R^{15}$, $R^{16}$, $R^{17}$ and $R^{18}$ independently of each other denote H or have one of the meanings of $R^3$ as defined above and below.

In a preferred embodiment of the present invention in formula D1 $R^{11}$ and $R^{12}$ denote H or F. In another preferred embodiment of the present invention in formulae D2, D5, D6, D8, D9 and D17 $R^1$ and $R^{12}$ denote H or F.

Further preferred are monomers and polymers of the present invention selected from the following list of preferred embodiments:
a=b=1, preferably in all repeating units,
a=1 and b=2, preferably in all repeating units,
a=2 and b=1, preferably in all repeating units,
a=b=2, preferably in all repeating units,
a and b have the same meaning, preferably in all repeating units,
$Ar^1$ and $Ar^2$ have the same meaning, preferably in all repeating units, n is at least 5, preferably at least 10, very preferably at least 50, and up to 2,000, preferably up to 500.

$M_W$ is at least 5,000, preferably at least 8,000, very preferably at least 10,000, and preferably up to 300,000, very preferably up to 100,000, $R^3$ and/or $R^4$ denote H, $R^3$ and/or $R^4$ are independently of each other selected from the group consisting of primary alkyl or alkoxy with 1 to 30 C atoms, secondary alkyl or alkoxy with 3 to 30 C atoms, and tertiary alkyl or alkoxy with 4 to 30 C atoms, wherein in all these groups one or more H atoms are optionally replaced by F, $R^0$ and $R^{00}$ are selected from H or $C_1$-$C_{10}$-alkyl, $R^5$ and $R^6$ are selected from halogen, —$CH_2Cl$, —CHO, —CH=$CH_2$—SiR'R"R''', —SnR'R"R''', —BR'R", —B(OR')(OR"), —B(OH)$_2$, $R^5$ and $R^6$ in formula III denote an endcap group selected from H, $C_1$-$C_{20}$-alkyl, $C_1$-$C_{20}$-alkoxy, $C_2$-$C_{20}$-alkenyl, $C_1$-$C_{20}$-fluoroalkyl and optionally substituted aryl or heteroaryl, $R^5$ and $R^6$ in formula IV are, preferably independently of each other, selected from the group consisting of Cl, Br, I, O-tosylate, O-triflate, O-mesylate, O-nonaflate, —SiMe$_2$F, —SiMeF$_2$, —O—SO$_2$Z$^1$, —B(OZ$^2$)$_2$, CZ$^3$=C(Z$^4$)$_2$, —C≡CH, —C≡CSi(Z)$_3$, —ZnX$^0$ and —Sn(Z$^4$)$_3$, wherein X$^0$ is halogen, Z$^{1-4}$ are selected from the group consisting of alkyl and aryl, each being optionally substituted, and two groups Z$^2$ may also form a cyclic group.

The polymers of the present invention can be synthesized according to or in analogy to methods that are known to the skilled person and are described in the literature. Other methods of preparation can be taken from the examples. For example, they can be suitably prepared by aryl-aryl coupling reactions, such as Yamamoto coupling, Suzuki coupling, Stille coupling, Sonogashira coupling, Heck coupling or Buchwald coupling. Suzuki coupling, Stille coupling and Yamamoto coupling are especially preferred.

The monomers which are polymerised to form the repeat units of the polymers can be prepared according to methods which are known to the person skilled in the art.

Preferably the polymers are prepared from monomers of formula Ia or its preferred embodiments as described above and below.

Another aspect of the invention is a process for preparing a polymer by coupling one or more identical or different monomeric units selected from formula IV or from formulae IV1-IV4 with one or more comonomers in a polymerisation reaction, preferably in an aryl-aryl coupling reaction.

Suitable and preferred comonomers are selected from the following formulae $R^5$—(Ar$^2$)$_d$-A-(Ar$^1$)$_c$—R$^6$     C $R^5$—(Ar$^1$)$_a$—R$^6$     D $R^5$—(Ar$^2$)$_b$—R$^6$     E wherein Ar$^1$, Ar$^2$, A, R$^5$, R$^6$, a, b, c and d are as defined in formula I2, II and IV.

Very preferred is a process for preparing a polymer by coupling one or more monomers selected from formula IV or formulae IV1-IV4 with one or more monomers of formula C, and optionally with one or more monomers selected from formula D and E, in an aryl-aryl coupling reaction.

For example, a first preferred embodiment of the present invention relates to a process of preparing a polymer by coupling a monomer of formula IV1

$R^5$—Ar$^1$—B—Ar$^2$—R$^6$     IV1 with a monomer of formula C1

$R^5$-A-R$^6$     C1 in an aryl-aryl coupling reaction.

A second preferred embodiment of the present invention relates to a process of preparing a polymer by coupling a monomer of formula IV2

$R^5$—B—R$^6$     IV2 with a monomer of formula C2

$R^5$—Ar$^2$-A-Ar'—R$^6$     C2 in an aryl-aryl coupling reaction.

A third preferred embodiment of the present invention relates to a process of preparing a polymer by coupling a monomer of formula IV2

$R^5$—B—R$^6$     IV2 with a monomer of formula C1

$R^5$-A-R$^6$     C1 and a monomer of formula D1

$R^5$—Ar$^1$—R$^6$     D1 in an aryl-aryl coupling reaction.

Preferred methods for polymerisation are those leading to C—C-coupling or C—N-coupling, like Suzuki polymerisation, as described for example in WO 00/53656, Yamamoto polymerisation, as described in for example in T. Yamamoto et al., *Progress in Polymer Science*, 1993, 17, 1153-1205 or in WO 2004/022626 A1, and Stille coupling, as described for example in Z. Bao et al., *J. Am. Chem. Soc.*, 1995, 117, 12426-12435. For example, when synthesizing a linear polymer by Yamamoto polymerisation, monomers as described above having two reactive halide groups R$^5$ and R$^6$ is preferably used. When synthesizing a linear polymer by Suzuki polymerisation, preferably a monomer as described above is used wherein at least one reactive group R$^5$ or R$^6$ is a boronic acid or boronic acid derivative group. When synthesizing a linear polymer by Stille polymerisation, preferably a monomer as described above is used wherein at least one reactive group R$^7$ or R$^8$ is a alkylstannane derivative group. Suzuki and Stille polymerisation may be used to prepare homopolymers as well as statistical, alternating and block random copolymers. Statistical or block copolymers can be prepared for example from the above monomers of formula V or its subformulae, wherein one of the reactive groups R$^5$ and R$^6$ is halogen and the other reactive group is a boronic acid, boronic acid derivative group or and alkylstannane. The synthesis of statistical, alternating and block copolymers is described in detail for example in WO 03/048225 A2 or WO 2005/014688 A2.

Suzuki and Stille polymerisation employs a Pd(0) complex or a Pd(II) salt. Preferred Pd(0) complexes are those bearing at least one phosphine ligand such as Pd(Ph$_3$P)$_4$. Another preferred phosphine ligand is tris(ortho-tolyl)phosphine, i.e. Pd(o-Tol$_3$P)$_4$. Preferred Pd(II) salts include palladium acetate, i.e. Pd(OAc)$_2$. Alternatively the Pd(0) complex can be prepared by mixing a Pd(0) dibenzylideneacetone complex, e.g. tris(dibenzylidene-acetone)dipalladium(0) bis(dibenzylideneacetone)palladium (0), or Pd(II) salts e.g. palladium acetate, with a phosphine ligand e.g. triphenyl-phosphine, tris(ortho-tolyl)phosphine or tri(tert-butyl)phosphine. Suzuki polymerisation is performed in the presence of a base, for example sodium carbonate, potassium carbonate, lithium hydroxide, potassium phosphate or an organic base such as tetraethylammonium carbonate or tetraethylammonium hydroxide. Yamamoto polymerisation employs a Ni(0) complex, for example bis(1,5-cyclooctadienyl) nickel(0).

As alternatives to halogens as described above, leaving groups of formula —O—SO$_2$Z$^1$ can be used wherein Z$^1$ is as described above. Particular examples of such leaving groups are tosylate, mesylate and triflate.

Especially suitable and preferred synthesis methods are illustrated in the synthesis schemes shown hereinafter, wherein R is an alkyl group, Ar is Ar$^1$ nd Ar$^1$, R$^1$, R$^2$, R$^3$, R$^4$, x, y and n are as defined in formulae I and II.

The synthesis of the 3,7-disubstituted benzo[1,2-b:4,5-b']dithiophene monomer is shown in Scheme 1. The synthesis of 3,7-diiodo-2,6-bis-trimethylsilanyl-benzo[1,2-b:4,5-b']dithiophene can be carried out following previously reported procedures, for example in C.-H. Wang, R.-R. Hu, S. Liang, J.-H. Chen, Z. Yang, J Pei, *Tet. Lett.* 2005, 46, 8153-8157.

The synthesis schemes for the alternating co-polymerisation of the 3,7-disubstituted benzo[1,2-b:4,5-b']dithiophene unit are shown in Scheme 2.

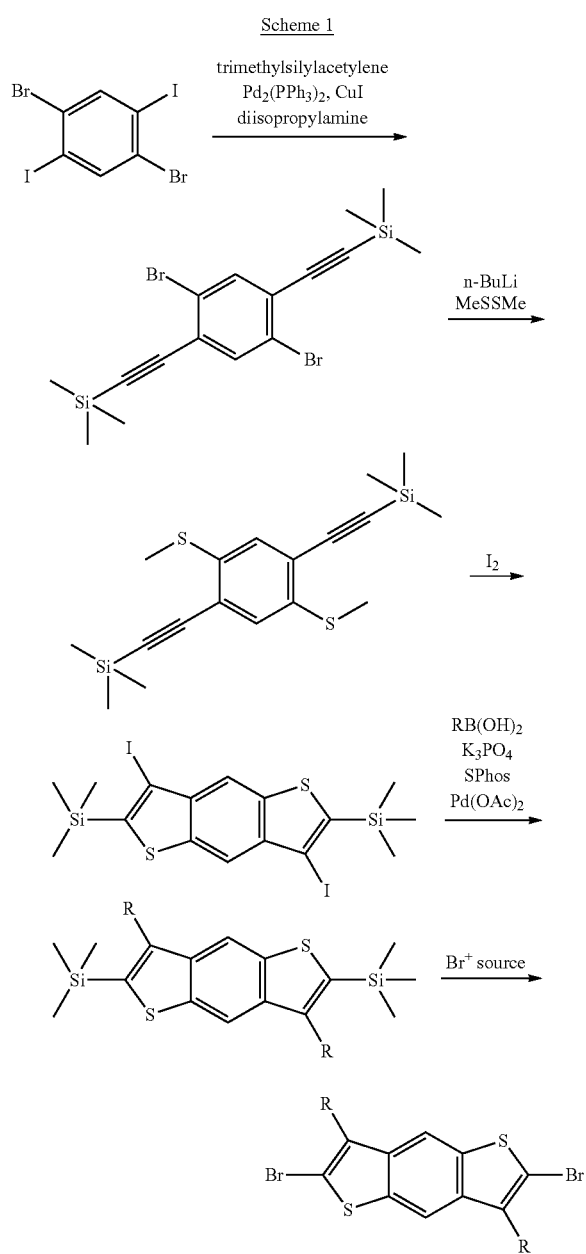

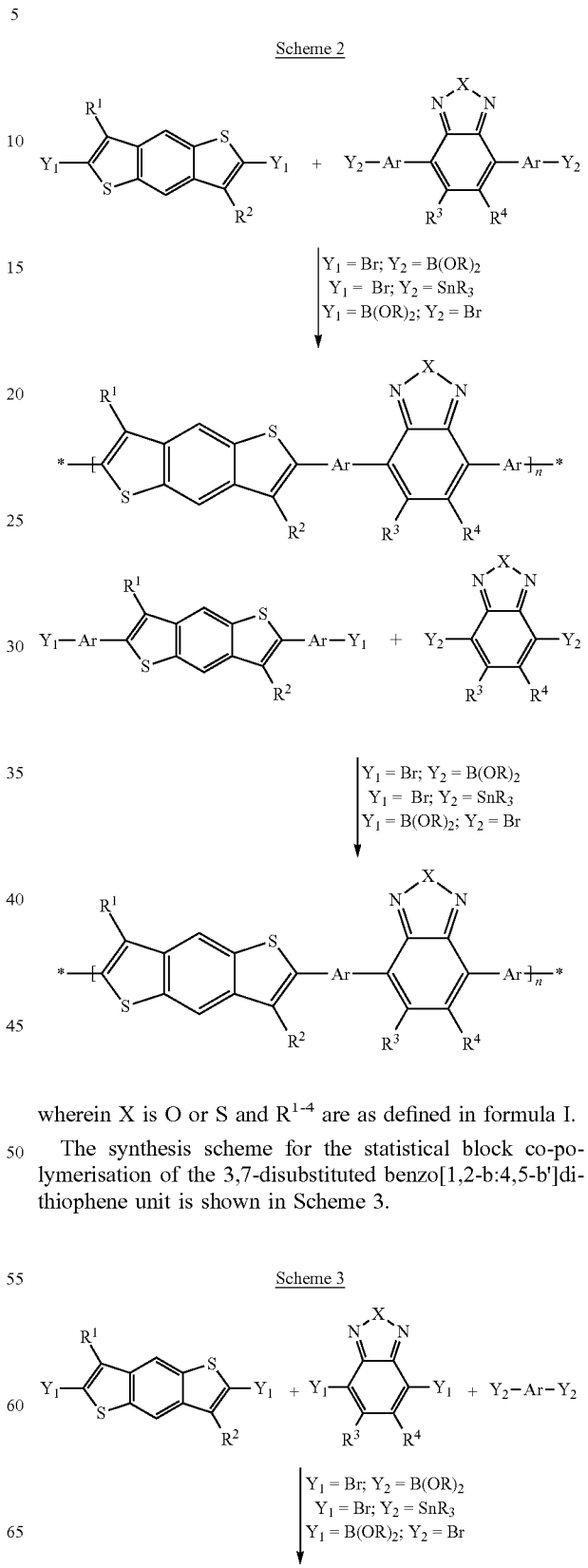

wherein X is O or S and R$^{1-4}$ are as defined in formula I.

The synthesis scheme for the statistical block co-polymerisation of the 3,7-disubstituted benzo[1,2-b:4,5-b']dithiophene unit is shown in Scheme 3.

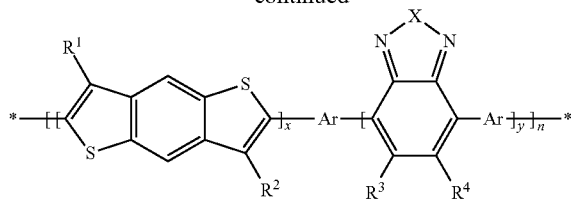

The novel methods of preparing monomers and polymers as described above and below are another aspect of the invention.

The polymers according to the present invention can also be used in mixtures or polymer blends, for example together with monomeric compounds or together with other polymers having charge-transport, semiconducting, electrically conducting, photoconducting and/or light emitting semiconducting properties, or for example with polymers having hole blocking or electron blocking properties for use as interlayers or charge blocking layers in OLED devices. Thus, another aspect of the invention relates to a polymer blend comprising one or more polymers according to the present invention and one or more further polymers having one or more of the above-mentioned properties. These blends can be prepared by conventional methods that are described in prior art and known to the skilled person. Typically the polymers are mixed with each other or dissolved in suitable solvents and the solutions combined.

Another aspect of the invention relates to a formulation comprising one or more polymers, mixtures or polymer blends as described above and below and one or more organic solvents.

Preferred solvents are aliphatic hydrocarbons, chlorinated hydrocarbons, aromatic hydrocarbons, ketones, ethers and mixtures thereof. Additional solvents which can be used include 1,2,4-trimethylbenzene, 1,2,3,4-tetra-methyl benzene, pentylbenzene, mesitylene, cumene, cymene, cyclohexylbenzene, diethylbenzene, tetralin, decalin, 2,6-lutidine, 2-fluoro-m-xylene, 3-fluoro-o-xylene, 2-chlorobenzotrifluoride, dimethylformamide, 2-chloro-6-fluorotoluene, 2-fluoroanisole, anisole, 2,3-dimethylpyrazine, 4-fluoroanisole, 3-fluoroanisole, 3-trifluoro-methylanisole, 2-methylanisole, phenetol, 4-methylanisole, 3-methylanisole, 4-fluoro-3-methylanisole, 2-fluorobenzonitrile, 4-fluoroveratrol, 2,6-dimethylanisole, 3-fluorobenzonitrile, 2,5-dimethylanisole, 2,4-dimethylanisole, benzonitrile, 3,5-dimethylanisole, N,N-dimethylaniline, ethyl benzoate, 1-fluoro-3,5-dimethoxy-benzene, 1-methylnaphthalene, N-methylpyrrolidinone, 3-fluorobenzotrifluoride, benzotrifluoride, benzotrifluoride, diosane, trifluoromethoxy-benzene, 4-fluorobenzotrifluoride, 3-fluoropyridine, toluene, 2-fluorotoluene, 2-fluorobenzotrifluoride, 3-fluorotoluene, 4-isopropylbiphenyl, phenyl ether, pyridine, 4-fluorotoluene, 2,5-difluorotoluene, 1-chloro-2,4-difluorobenzene, 2-fluoropyridine, 3-chlorofluorobenzene, 3-chlorofluorobenzene, 1-chloro-2,5-difluorobenzene, 4-chlorofluorobenzene, chlorobenzene, o-dichlorobenzene, 2-chlorofluorobenzene, p-xylene, m-xylene, o-xylene or mixture of o-, m-, and p-isomers. Solvents with relatively low polarity are generally preferred. For inkjet printing solvents and solvent mixtures with high boiling temperatures are preferred. For spin coating alkylated benzenes like xylene and toluene are preferred.

Examples of especially preferred solvents include, without limitation, dichloromethane, trichloromethane, monochlorobenzene, o-dichlorobenzene, tetrahydrofuran, anisole, morpholine, toluene, o-xylene, m-xylene, p-xylene, 1,4-dioxane, acetone, methylethylketone, 1,2-dichloroethane, 1,1,1-trichloroethane, 1,1,2,2-tetrachloroethane, ethyl acetate, n-butyl acetate, dimethylformamide, dimethylacetamide, dimethylsulfoxide, tetraline, decaline, indane, methyl benzoate, ethyl benzoate, mesitylene and/or mixtures thereof.

The concentration of the polymers in the solution is preferably 0.1 to 10% by weight, more preferably 0.5 to 5% by weight. Optionally, the solution also comprises one or more binders to adjust the rheological properties, as described for example in WO 2005/055248 A1.

After the appropriate mixing and ageing, solutions are evaluated as one of the following categories: complete solution, borderline solution or insoluble. The contour line is drawn to outline the solubility parameter-hydrogen bonding limits dividing solubility and insolubility. 'Complete' solvents falling within the solubility area can be chosen from literature values such as published in "Crowley, J. D., Teague, G. S. Jr and Lowe, J. W. Jr., Journal of Paint Technology, 1966, 38 (496), 296". Solvent blends may also be used and can be identified as described in "Solvents, W. H. Ellis, Federation of Societies for Coatings Technology, p 9-10, 1986". Such a procedure may lead to a blend of 'non' solvents that will dissolve both the polymers of the present invention, although it is desirable to have at least one true solvent in a blend.

The polymers according to the present invention can also be used in patterned OSC layers in the devices as described above and below. For applications in modern microelectronics it is generally desirable to generate small structures or patterns to reduce cost (more devices/unit area), and power consumption. Patterning of thin layers comprising a polymer according to the present invention can be carried out for example by photolithography, electron beam lithography or laser patterning.

For use as thin layers in electronic or electrooptical devices the polymers, polymer blends or formulations of the present invention may be deposited by any suitable method. Liquid coating of devices is more desirable than vacuum deposition techniques. Solution deposition methods are especially preferred. The formulations of the present invention enable the use of a number of liquid coating techniques. Preferred deposition techniques include, without limitation, dip coating, spin coating, ink jet printing, nozzle printing, letter-press printing, screen printing, gravure printing, doctor blade coating, roller printing, reverse-roller printing, offset lithography printing, dry offset lithography printing, flexographic printing, web printing, spray coating, dip coating, curtain coating, brush coating, slot dye coating or pad printing.

Ink-jet printing is particularly preferred when high resolution layers and devices needs to be prepared. Selected formulations of the present invention may be applied to prefabricated device substrates by ink jet printing or microdispensing. Preferably industrial piezoelectric print heads such as but not limited to those supplied by Aprion, Hitachi-Koki, InkJet Technology, On Target Technology, Picojet, Spectra, Trident, Xaar may be used to apply the organic semiconductor layer to a substrate. Additionally semi-industrial heads such as those manufactured by Brother, Epson, Konica, Seiko Instruments Toshiba TEC or single nozzle microdispensers such as those produced by Microdrop and Microfab may be used.

In order to be applied by ink jet printing or microdispensing, the polymers should be first dissolved in a suitable solvent. Solvents must fulfil the requirements stated above and must not have any detrimental effect on the chosen print head. Additionally, solvents should have boiling points >100° C., preferably >140° C. and more preferably >150° C. in order to prevent operability problems caused by the solution drying out inside the print head. Apart from the solvents mentioned above, suitable solvents include substituted and non-substituted xylene derivatives, di-$C_{1-2}$-alkyl formamide, substituted and non-substituted anisoles and other phenol-ether derivatives, substituted heterocycles such as substituted pyridines, pyrazines, pyrimidines, pyrrolidinones, substituted and non-substituted N,N-di-$C_{1-2}$-alkylanilines and other fluorinated or chlorinated aromatics.

A preferred solvent for depositing a polymer according to the present invention by ink jet printing comprises a benzene derivative which has a benzene ring substituted by one or more substituents wherein the total number of carbon atoms among the one or more substituents is at least three. For example, the benzene derivative may be substituted with a propyl group or three methyl groups, in either case there being at least three carbon atoms in total. Such a solvent enables an ink jet fluid to be formed comprising the solvent with the polymer, which reduces or prevents clogging of the jets and separation of the components during spraying. The solvent(s) may include those selected from the following list of examples: dodecylbenzene, 1-methyl-4-tert-butylbenzene, terpineol limonene, isodurene, terpinolene, cymene, diethylbenzene. The solvent may be a solvent mixture, that is a combination of two or more solvents, each solvent preferably having a boiling point >100° C., more preferably >140° C. Such solvent(s) also enhance film formation in the layer deposited and reduce defects in the layer.

The ink jet fluid (that is mixture of solvent, binder and semiconducting compound) preferably has a viscosity at 20° C. of 1-100 mPa·s, more preferably 1-50 mPa·s and most preferably 1-30 mPa·s.

The polymers or formulations according to the present invention can additionally comprise one or more further components or additives selected for example from surface-active compounds, lubricating agents, wetting agents, dispersing agents, hydrophobing agents, adhesive agents, flow improvers, defoaming agents, deaerators, diluents which may be reactive or non-reactive, auxiliaries, colourants, dyes or pigments, sensitizers, stabilizers, nanoparticles or inhibitors.

The polymers according to the present invention are useful as charge transport, semiconducting, electrically conducting, photoconducting or light emitting materials in optical, electrooptical, electronic, electroluminescent or photoluminescent components or devices. In these devices, the polymers of the present invention are typically applied as thin layers or films.

Thus, the present invention also provides the use of the semiconducting polymer, polymers blend, formulation or layer in an electronic device. The formulation may be used as a high mobility semiconducting material in various devices and apparatus. The formulation may be used, for example, in the form of a semiconducting layer or film. Accordingly, in another aspect, the present invention provides a semiconducting layer for use in an electronic device, the layer comprising a polymer, polymer blend or formulation according to the invention. The layer or film may be less than about 30 microns. For various electronic device applications, the thickness may be less than about 1 micron thick. The layer may be deposited, for example on a part of an electronic device, by any of the aforementioned solution coating or printing techniques.

The invention additionally provides an electronic device comprising a polymer, polymer blend, formulation or organic semiconducting layer according to the present invention. Especially preferred devices are OFETs, TFTs, ICs, logic circuits, capacitors, RFID tags, OLEDs, OLETs, OPEDs, OPVs, solar cells, laser diodes, photoconductors, photodetectors, electrophotographic devices, electrophotographic recording devices, organic memory devices, sensor devices, charge injection layers, Schottky diodes, planarising layers, antistatic films, conducting substrates and conducting patterns.

Especially preferred electronic device are OFETs, OLEDs and OPV devices, in particular bulk heterojunction (BHJ) OPV devices. In an OFET, for example, the active semiconductor channel between the drain and source may comprise the layer of the invention. As another example, in an OLED device, the charge (hole or electron) injection or transport layer may comprise the layer of the invention.

For use in OPV devices the polymer according to the present invention is preferably used as photo-active layer. This implies the use in a formulation that comprises or contains, more preferably consists essentially of, very preferably exclusively of, a p-type (electron donor) semiconductor and an n-type (electron acceptor) semiconductor. The p-type semiconductor is constituted by a polymer according to the present invention. The n-type semiconductor can be an inorganic material such as zinc oxide or cadmium selenide, or an organic material such as a fullerene derivate, for example (6,6)-phenyl-butyric acid methyl ester derivatized methano $C_{60}$ fullerene, also known as "PCBM" or "$C_{60}$PCBM", as disclosed for example in G. Yu, J. Gao, J. C. Hummelen, F. Wudl, A. J. Heeger, *Science*, 1995, 270, 1789 and having the structure shown below, or an structural analogous compound with e.g. a $C_{70}$ fullerene group ($C_{70}$PCBM), or a polymer (see for example Coakley, K. M. and McGehee, M. D. *Chem. Mater.*, 2004, 16, 4533).

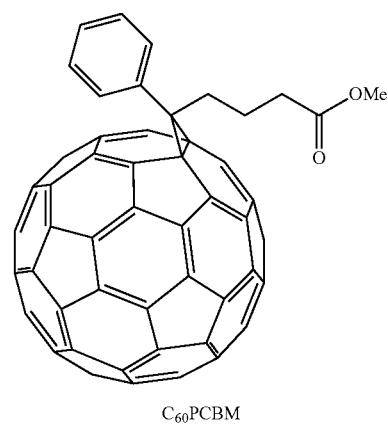 [SMILES: COC(=O)CCCC1(c2ccccc2)C23C=C4Cc5cc6cc7c8c9c(cc%10cc%11c%12c(c%13c%14c%15c(c4c5c4c6c8c(c%154)c4c9c%10c%12c%144)C%1321)C(=C3)C%11)C7]

$C_{60}$PCBM

A blend or mixture of a polymer according to the present invention with a $C_{60}$ or $C_{70}$ fullerene or modified fullerene like $C_{60}$PCBM or $C_{70}$PCBM is the preferred material combination to be used in formulations for OPV devices. Preferably the ratio polymer:fullerene is from 5:1 to 1:5 by weight, more preferably from 1:1 to 1:3 by weight, most preferably 1:1 to 1:2 by weight. A polymeric binder may also be included, from 5 to 95% by weight. Examples of binder include polystyrene (PS), polypropylene (PP) and polymethylmethacrylate (PMMA).

To produce thin layers in BHJ OPV devices the polymers, polymer blends or formulations of the present invention may be deposited by any suitable method. Liquid coating of devices is more desirable than vacuum deposition techniques. Solution deposition methods are especially preferred. The formulations of the present invention enable the use of a number of liquid coating techniques. Preferred deposition techniques include, without limitation, dip coating, spin coating, ink jet printing, nozzle printing, letterpress printing, screen printing, gravure printing, doctor blade coating, roller printing, reverse-roller printing, offset lithography printing, dry offset lithography printing, flexographic printing, web printing, spray coating, dip coating, curtain coating, brush coating, slot dye coating or pad printing. For the fabrication of OPV devices and modules area printing method compatible with flexible substrates are preferred, for example slot dye coating, spray coating and the like.

Suitable solutions or formulations containing the blend or mixture of a polymer according to the present invention with a $C_{60}$ or $C_{70}$ fullerene or modified fullerene like PCBM must be prepared. In the preparation of formulations, suitable solvent must be selected to ensure full dissolution of both component, p-type and n-type and take into account the boundary conditions (for example rheological properties) introduced by the chosen printing method.

Organic solvent are generally used for this purpose. Typical solvents can be aromatic solvents, halogenated solvents or chlorinated solvents, including chlorinated aromatic solvents. Examples include, but are not limited to chlorobenzene, 1,2-dichlorobenzene, chloroform, 1,2-dichloroethane, dichloromethane, carbon tetrachloride, toluene, cyclohexanone, ethylacetate, tetrahydrofuran, anisole, morpholine, o-xylene, m-xylene, p-xylene, 1,4-dioxane, acetone, methylethylketone, 1,2-dichloroethane, 1,1,1-trichloroethane, 1,1,2,2-tetrachloroethane, ethyl acetate, n-butyl acetate, dimethylformamide, dimethylacetamide, dimethylsulfoxide, tetraline, decaline, indane, methyl benzoate, ethyl benzoate, mesitylene and combinations thereof.

The OPV device can for example be of any type known from the literature (see e.g. Waldauf et al., *Appl. Phys. Lett.*, 2006, 89, 233517).

A first preferred OPV device according to the invention comprises the following layers (in the sequence from bottom to top):
- optionally a substrate,
- a high work function electrode, preferably comprising a metal oxide, like for example ITO, serving as anode,
- an optional conducting polymer layer or hole transport layer, preferably comprising an organic polymer or polymer blend, for example of PEDOT:PSS (poly(3,4-ethylenedioxythiophene): poly(styrene-sulfonate), or TBD (N,N'-dyphenyl-N—N'-bis(3-methylphenyl)-1,1'biphenyl-4,4'-diamine) or NBD (N,N'-dyphenyl-N—N'-bis(1-napthylphenyl)-1,1'biphenyl-4,4'-diamine),
- a layer, also referred to as "active layer", comprising a p-type and an n-type organic semiconductor, which can exist for example as a p-type/n-type bilayer or as distinct p-type and n-type layers, or as blend or p-type and n-type semiconductor, forming a BHJ,
- optionally a layer having electron transport properties, for example comprising LiF,
- a low work function electrode, preferably comprising a metal like for example aluminum, serving as cathode, wherein at least one of the electrodes, preferably the anode, is transparent to visible light, and
- wherein the p-type semiconductor is a polymer according to the present invention.

A second preferred OPV device according to the invention is an inverted OPV device and comprises the following layers (in the sequence from bottom to top):
- optionally a substrate,
- a high work function metal or metal oxide electrode, comprising for example ITO, serving as cathode,
- a layer having hole blocking properties, preferably comprising a metal oxide like $TiO_x$ or $Zn_x$,
- an active layer comprising a p-type and an n-type organic semiconductor, situated between the electrodes, which can exist for example as a p-type/n-type bilayer or as distinct p-type and n-type layers, or as blend or p-type and n-type semiconductor, forming a BHJ,
- an optional conducting polymer layer or hole transport layer, preferably comprising an organic polymer or polymer blend, for example of PEDOT:PSS or TBD or NBD,
- an electrode comprising a high work function metal like for example silver, serving as anode,
- wherein at least one of the electrodes, preferably the cathode, is transparent to visible light, and
- wherein the p-type semiconductor is a polymer according to the present invention.

In the OPV devices of the present invent invention the p-type and n-type semiconductor materials are preferably selected from the materials, like the polymer/fullerene systems, as described above When the active layer is deposited on the substrate, it forms a BHJ that phase separate at nanoscale level. For discussion on nanoscale phase separation see Dennler et al, *Proceedings of the IEEE*, 2005, 93 (8), 1429 or Hoppe et al, *Adv. Func. Mater,* 2004, 14(10), page 1005. An optional annealing step may be then necessary to optimize blend morphology and consequently OPV device performance.

Another method to optimize device performance is to prepare formulations for the fabrication of OPV(BHJ) devices that may include high boiling point additives to promote phase separation in the right way. 1,8-octanedithiol, 1,8-diiodooctane, nitrobenzene, chloronaphthalene, and other additives have been used to obtain high-efficiency solar cells. Examples are disclosed in J. Peet, et al, *Nat. Mater.*, 2007, 6, 497 or Fréchet et al. *J. Am. Chem. Soc.*, 2010, 132, 7595-7597.

The compounds formulations and layers of the present invention are also suitable for use in an OFET as the semiconducting channel. Accordingly, the invention also provides an OFET comprising a gate electrode, an insulating (or gate insulator) layer, a source electrode, a drain electrode and an organic semiconducting channel connecting the source and drain electrodes, wherein the organic semiconducting channel comprises a polymer, polymer blend, formulation or organic semiconducting layer according to the present invention. Other features of the OFET are well known to those skilled in the art.

OFETs where an OSC material is arranged as a thin film between a gate dielectric and a drain and a source electrode, are generally known, and are described for example in U.S. Pat. No. 5,892,244, U.S. Pat. No. 5,998,804, U.S. Pat. No. 6,723,394 and in the references cited in the background section. Due to the advantages, like low cost production using the solubility properties of the compounds according to the invention and thus the processibility of large surfaces, preferred applications of these FETs are such as integrated circuitry, TFT displays and security applications.

The gate, source and drain electrodes and the insulating and semiconducting layer in the OFET device may be arranged in any sequence, provided that the source and drain electrode are separated from the gate electrode by the insulating layer, the gate electrode and the semiconductor layer both contact the insulating layer, and the source electrode and the drain electrode both contact the semiconducting layer.

An OFET device according to the present invention preferably comprises:
 a source electrode,
 a drain electrode,
 a gate electrode,
 a semiconducting layer,
 one or more gate insulator layers,
 optionally a substrate.
wherein the semiconductor layer preferably comprises a polymer, polymer blend or formulation as described above and below.

The OFET device can be a top gate device or a bottom gate device. Suitable structures and manufacturing methods of an OFET device are known to the skilled in the art and are described in the literature, for example in US 2007/0102696 A1.

The gate insulator layer preferably comprises a fluoropolymer, like e.g. the commercially available Cytop 809M® or Cytop 107M® (from Asahi Glass). Preferably the gate insulator layer is deposited, e.g. by spin-coating, doctor blading, wire bar coating, spray or dip coating or other known methods, from a formulation comprising an insulator material and one or more solvents with one or more fluoro atoms (fluorosolvents), preferably a perfluorosolvent. A suitable perfluorosolvent is e.g. FC75® (available from Acros, catalogue number 12380). Other suitable fluoropolymers and fluorosolvents are known in prior art, like for example the perfluoropolymers Teflon AF® 1600 or 2400 (from DuPont) or Fluoropel® (from Cytonix) or the perfluorosolvent FC 43® (Acros, No. 12377). Especially preferred are organic dielectric materials having a low permittivity (or dielectric constant) from 1.0 to 5.0, very preferably from 1.8 to 4.0 ("low k materials"), as disclosed for example in US 2007/0102696 A1 or U.S. Pat. No. 7,095,044.

In security applications, OFETs and other devices with semiconducting materials according to the present invention, like transistors or diodes, can be used for RFID tags or security markings to authenticate and prevent counterfeiting of documents of value like banknotes, credit cards or ID cards, national ID documents, licenses or any product with monetary value, like stamps, tickets, shares, cheques etc.

Alternatively, the materials according to the invention can be used in OLEDs, e.g. as the active display material in a flat panel display applications, or as backlight of a flat panel display like e.g. a liquid crystal display. Common OLEDs are realized using multilayer structures. An emission layer is generally sandwiched between one or more electron-transport and/or hole-transport layers. By applying an electric voltage electrons and holes as charge carriers move towards the emission layer where their recombination leads to the excitation and hence luminescence of the lumophor units contained in the emission layer. The inventive compounds, materials and films may be employed in one or more of the charge transport layers and/or in the emission layer, corresponding to their electrical and/or optical properties. Furthermore their use within the emission layer is especially advantageous, if the compounds, materials and films according to the invention show electroluminescent properties themselves or comprise electroluminescent groups or compounds. The selection, characterization as well as the processing of suitable monomeric, oligomeric and polymeric compounds or materials for the use in OLEDs is generally known by a person skilled in the art, see, e.g., Müller et al, *Synth. Metals,* 2000, 111-112, 31-34, Alcala, *J. Appl. Phys.,* 2000, 88, 7124-7128 and the literature cited therein.

According to another use, the materials according to this invention, especially those showing photoluminescent properties, may be employed as materials of light sources, e.g. in display devices, as described in EP 0 889 350 A1 or by C. Weder et al., *Science,* 1998, 279, 835-837.

A further aspect of the invention relates to both the oxidised and reduced form of the compounds according to this invention. Either loss or gain of electrons results in formation of a highly delocalised ionic form, which is of high conductivity. This can occur on exposure to common dopants. Suitable dopants and methods of doping are known to those skilled in the art, e.g. from EP 0 528 662, U.S. Pat. No. 5,198,153 or WO 96/21659.

The doping process typically implies treatment of the semiconductor material with an oxidating or reducing agent in a redox reaction to form delocalised ionic centres in the material, with the corresponding counterions derived from the applied dopants. Suitable doping methods comprise for example exposure to a doping vapor in the atmospheric pressure or at a reduced pressure, electrochemical doping in a solution containing a dopant, bringing a dopant into contact with the semiconductor material to be thermally diffused, and ion-implantantion of the dopant into the semiconductor material.

When electrons are used as carriers, suitable dopants are for example halogens (e.g., $I_2$, $Cl_2$, $Br_2$, ICl, $ICl_3$, IBr and IF), Lewis acids (e.g., $PF_5$, $AsF_5$, $SbF_5$, $BF_3$, $BCl_3$, $SbCl_5$, $BBr_3$ and $SO_3$), protonic acids, organic acids, or amino acids (e.g., HF, HCl, $HNO_3$, $H_2SO_4$, $HClO_4$, $FSO_3H$ and $ClSO_3H$), transition metal compounds (e.g., $FeCl_3$, FeOCl, $Fe(ClO_4)_3$, $Fe(4-CH_3C_6H_4SO_3)_3$, $TiCl_4$, $ZrCl_4$, $HfCl_4$, $NbF_5$, $NbCl_5$, $TaCl_5$, $MoF_5$, $MoCl_5$, $WF_5$, $WCl_6$, $UF_6$ and $LnCl_3$ (wherein Ln is a lanthanoid), anions (e.g., $Cl^-$, $Br^-$, $I^-$, $I_3^-$, $HSO_4^-$, $SO_4^{2-}$, $NO_3^-$, $ClO_4^-$, $BF_4^-$, $PF_6^-$, $AsF_6^-$, $SbF_6^-$, $FeCl_4^-$, $Fe(CN)_6^{3-}$, and anions of various sulfonic acids, such as aryl-$SO_3$). When holes are used as carriers, examples of dopants are cations (e.g., $H^+$, $Li^+$, $Na^+$, $K^+$, $Rb^+$ and $Cs^+$), alkali metals (e.g., Li, Na, K, Rb, and Cs), alkaline-earth metals (e.g., Ca, Sr, and Ba), $O_2$, $XeOF_4$, ($NO_2^+$) ($SbF_6^-$), ($NO_2^+$) ($SbCl_6^-$), ($NO_2^+$) ($BF_4$—), $AgClO_4$, $H_2IrCl_6$, $La(NO_3)_3 \cdot 6H_2O$, $FSO_2OOSO_2F$, Eu, acetylcholine, $R_4N^+$, (R is an alkyl group), $R_4P^+$ (R is an alkyl group), $R_6As^+$ (R is an alkyl group), and $R_3S^+$ (R is an alkyl group).

The conducting form of the compounds of the present invention can be used as an organic "metal" in applications including, but not limited to, charge injection layers and ITO planarising layers in OLED applications, films for flat panel displays and touch screens, antistatic films, printed conductive substrates, patterns or tracts in electronic applications such as printed circuit boards and condensers.

The compounds and formulations according to the present invention amy also be suitable for use in organic plasmon-emitting diodes (OPEDs), as described for example in Koller et al., *Nat. Photonics,* 2008, 2, 684.

According to another use, the materials according to the present invention can be used alone or together with other materials in or as alignment layers in LCD or OLED devices, as described for example in US 2003/0021913. The use of charge transport compounds according to the present invention can increase the electrical conductivity of the alignment layer. When used in an LCD, this increased electrical conductivity can reduce adverse residual dc effects in the switchable LCD cell and suppress image sticking or, for example in ferroelectric LCDs, reduce the residual charge produced by the switching of the spontaneous polarisation charge of the ferroelectric LCs. When used in an OLED device comprising a light emitting material provided onto the alignment layer, this increased electrical conductivity can enhance the electroluminescence of the light emitting material. The compounds or materials according to the present invention having mesogenic or liquid crystalline properties can form oriented anisotropic films as described above, which are especially useful as alignment layers to induce or enhance alignment in a liquid crystal medium provided onto said anisotropic film. The materials according to the present invention may also be combined with photoisomerisable compounds and/or chromophores for use in or as photoalignment layers, as described in US 2003/0021913 A1.

According to another use the materials according to the present invention, especially their water-soluble derivatives (for example with polar or ionic side groups) or ionically doped forms, can be employed as chemical sensors or materials for detecting and discriminating DNA sequences. Such uses are described for example in L. Chen, D. W. McBranch, H. Wang, R. Helgeson, F. Wudl and D. G. Whitten, *Proc. Natl. Acad. Sci. U.S.A.*, 1999, 96, 12287; D. Wang, X. Gong, P. S. Heeger, F. Rininsland, G. C. Bazan and A. J. Heeger, *Proc. Natl. Acad. Sci. U.S.A.*, 2002, 99, 49; N. DiCesare, M. R. Pinot, K. S. Schanze and J. R. Lakowicz, *Langmuir*, 2002, 18, 7785; D. T. McQuade, A. E. Pullen, T. M. Swager, *Chem. Rev.*, 2000, 100, 2537.

Unless the context clearly indicates otherwise, as used herein plural forms of the terms herein are to be construed as including the singular form and vice versa. Above and below, unless stated otherwise percentages are percent by weight and temperatures are given in degrees Celsius.

Throughout the description and claims of this specification, the words "comprise" and "contain" and variations of the words, for example "comprising" and "comprises", mean "including but not limited to", and are not intended to (and do not) exclude other components.

It will be appreciated that variations to the foregoing embodiments can be made while still falling within the scope of the invention. Each feature disclosed in this specification, unless stated otherwise, may be replaced by alternative features serving the same, equivalent or similar purpose. Thus, unless stated otherwise, each feature disclosed is one example only of a generic series of equivalent or similar features.

All of the features disclosed in this specification may be combined in any combination, except combinations where at least some of such features and/or steps are mutually exclusive. In particular, the preferred features of the invention are applicable to all aspects of the invention and may be used in any combination. Likewise, features described in non-essential combinations may be used separately (not in combination).

The invention will now be described in more detail by reference to the following examples, which are illustrative only and do not limit the scope of the invention.

Example 1

Monomer 1,4-Dibromo-2,5-bis-trimethylsilanylethynyl-benzene

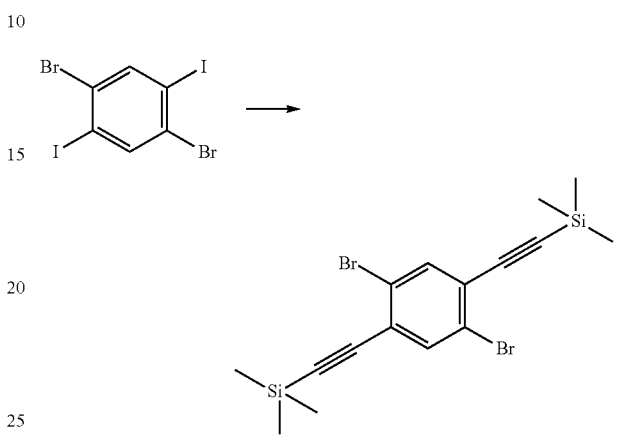

To a degassed solution of 1,4-dibromo-2,5-diiodo-benzene (60.0 g, 123 mmol) in diisopropylamine (174 cm$^3$, 1230 mmol) and THF (600 cm$^3$) at 23° C. is added trimethylsilylacetylene (35 cm$^3$, 250 mmol) and Pd$_2$(PPh$_3$)$_2$Cl$_2$ (433 mg, 0.615 mmol) followed by CuI (234 mg, 1.23 mmol). The reaction mixture is stirred at 23° C. for 24 hours before being poured into aqueous citric acid (250 cm$^3$, 10% w/w) and extracted with diethyl ether (3×300 cm$^3$). The combined organic layers are washed with water and brine, dried over magnesium sulfate and concentrated in vacuo to give a dark orange oily residue which is purified by column chromatography on silica gel (eluent: petroleum ether 40-60). The resulting pale yellow oil becomes solid at room temperature and is triturated in cooled petroleum ether 40-60 to give a pale yellow solid (38.00 g, 88.72 mmol, 72%). $^1$H NMR (300 MHz, CDCl$_3$): 0.28 (18H, s, CH$_3$), 7.68 (2H, s, ArH).

1,4-Bis-methylsulfanyl-2,5-bis-trimethylsilanylethynyl-benzene

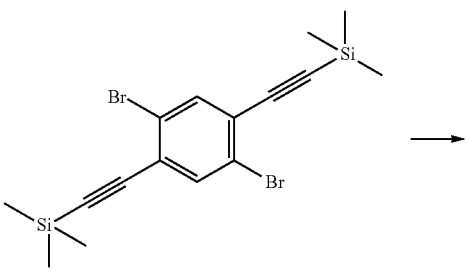

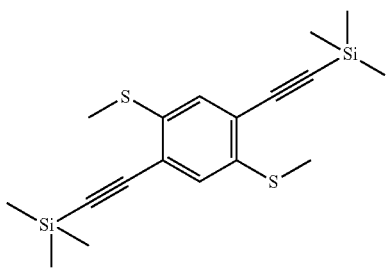

To a solution of 1,4-dibromo-2,5-bis-trimethylsilanylethynylbenzene (5.00 g, 11.7 mmol) in diethyl ether (300 cm³) at −78° C. is added dropwise n-BuLi (16.3 cm³, 2.5 M in hexanes, 40.8 mmol) and the reaction is stirred for 10 minutes before being allowed to warm to 23° C. and then stirred for a further 1 hour. Methyldisulfanylmethane (4.2 cm³, 46 mmol) is added dropwise and the solution is stirred at 23° C. overnight. The reaction mixture is poured into ammonium chloride (sat aq.), the organic layer is washed with ammonium chloride and brine, dried over sodium sulfate and concentrated in vacuo. The residue is purified by column chromatography on silica gel (eluent: 0-20% dichloromethane/petroleum ether 40-60) to give a yellow solid (3.22 g, 8.88 mmol, 76%). $^1$H NMR (300 MHz, CDCl$_3$): 0.29 (18H, s, Si(CH$_3$)$_3$), 2.48 (6H, s, SCH$_3$), 7.17 (2H, s, ArH).

3,7-Diiodo-2,6-bis(trimethylsilyl)benzo[1,2-b;4,5-b']dithiophene

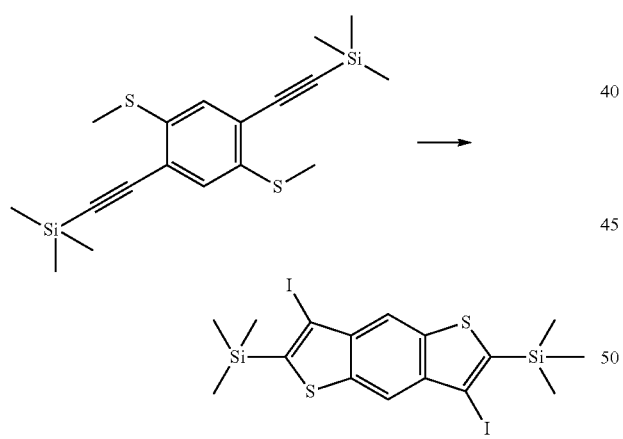

To a solution of 1,4-bis(methylsulfanyl)-2,5-bis(trimethylsilylethynyl)benzene (3.20 g, 8.82 mmol) in CH$_2$Cl$_2$ (300 cm³) is added iodine (8.96 g, 35.3 mmol) and the reaction mixture is flushed with nitrogen for 30 minutes and then stirred at 23° C. for 4 hours. The excess iodine is removed by washing with sodium thiosulfate and the aqueous layer is extracted with diethyl ether (2×50 cm³). The combined organic layers are dried over magnesium sulfate and concentrated in vacuo. The residue is then passed through a silica plug eluting with diethyl ether to give a white solid (4.50 g, 7.67 mmol, 87%). $^1$H NMR (300 MHz, CDCl$_3$): 0.55 (18H, s, Si(CH$_3$)$_3$), 8.26 (2H, s, ArH).

3,7-Didodecyl-2,6-bis(trimethylsilyl)benzo[1,2-b;4,5-b']dithiophene

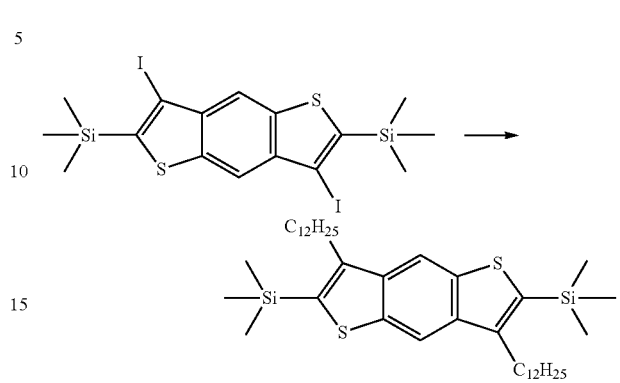

3,7-Diiodo-2,6-bis(trimethylsilyl)benzo[1,2-b;4,5-b']dithiophene (2.16 g, 3.68 mmol), dodecyl boronic acid (3.94 g, 18.4 mmol), K$_3$PO$_4$·H$_2$O (6.79 g, 29.5 mmol) and SPhos (121 mg, 0.295 mmol) are dissolved in toluene (150 cm³) and the mixture is degassed with nitrogen for 30 minutes. Pd(OAc)$_2$ (33 mg, 0.15 mmol) is then added and the solution is heated at 100° C. overnight with vigorous stirring. The cooled reaction mixture is filtered through a pad of silica and eluted with diethyl ether. The filtrate is concentrated in vacuo and the residue is recrystallised from methanol to give a pale yellow solid (1.26 g, 1.83 mmol, 50%). $^1$H NMR (300 MHz, CDCl$_3$): 0.43 (18H, s, Si(CH$_3$)$_3$), 0.89 (6H, dd, CH$_3$, J=6.9, 6.5 Hz), 1.20-1.43 (32H, m, CH$_2$), 1.44-1.61 (4H, m, CH$_2$), 1.63-1.76 (4H, m, CH$_2$), 2.94 (4H, dd, ArCH$_2$, J=8.3, 8.0 Hz), 8.15 (2H, s, ArH).

2,6-Dibromo-3,7-didodecylbenzo[1,2-b;4,5-b']dithiophene

To a solution of 3,7-didodecyl-2,6-bis(trimethylsilyl)benzo[1,2-b;4,5-b']dithiophene (1.10 g, 1.63 mmol) in tetrahydrofuran (40 cm³) is added bromine (0.17 cm³, 3.3 mmol) and the reaction is protected from light and stirred at 23° C. for 30 minutes. The reaction mixture is poured into water and extracted into diethyl ether. The combined organic layers are dried over magnesium sulfate and concentrated in vacuo. The residue is purified by column chromatography (silica, eluent petroleum ether) and by recrystallisation from a mixture of tetrahydrofuran and acetonitrile to give a white crystalline solid (650 mg, 0.949 mmol, 58%). $^1$H NMR (300 MHz, CDCl$_3$): 0.89 (6H, t, CH$_3$, J=6.9 Hz), 1.13-1.51 (36H, m, CH$_2$), 1.58-1.74 (4H, m, CH$_2$), 2.87 (4H, dd, ArCH$_2$, J=7.9, 7.5 Hz), 7.98 (2H, s, ArH).

Example 2

Polymers

The polymers 2.1 to 2.4 were synthesized according to the following general procedure: 2,6-dibromo-3,7-didodecyl-benzo[1,2-b;4,5-b']dithiophene (0.5 eq), thiophene based co-monomer (1.0 eq), 4,7-dibromo-5,6-bis-octyloxy-benzo-2,1,3-thiadiazole or 4,7-dibromo-5,6-bis-octyloxy-benzo-2,1,3-oxadiazole (0.5 eq), P(o-tol)$_3$ (0.08 eq) and Pd$_2$(dba)$_3$ (0.02 eq) are placed in a microwave tube which is then purged with nitrogen 3 times. Degassed chlorobenzene (6.25 cm$^3$/eq) is added and the mixture is purged with nitrogen for 5 minutes. The reaction mixture is placed in a microwave reactor (Biotage AG Initiator) and heated sequentially at 140° C. (60 seconds), 160° C. (60 seconds) and 170° C. (1800 seconds). Immediately after completion of the reaction, the reaction mixture is allowed to cool to room temperature and is precipitated into stirred methanol (100 cm$^3$) with methanol washings (2×10 cm$^3$) of the reaction tube. The mixture is stirred for 10 minutes and the polymer is collected by filtration and is washed with methanol (100 cm$^3$) to give a black solid. The crude is subjected to Soxhlet extraction with acetone, petroleum ether 40-60, cyclohexane, chloroform and chlorobenzene. The chloroform or chlorobenzene fraction is precipitated into stirred methanol (400 cm$^3$) and the polymer is collected by filtration.

Poly{[2,6-(2-thienyl)-3,7-di(dodecyl)benzo[1,2-b:4,5-b']dithiophene]-co-4,7-(2-thien-5-yl)-5,6-dioctyloxy-2,1,3-benzothiadiazole}(2.1)

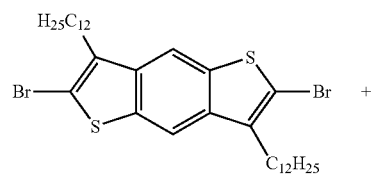

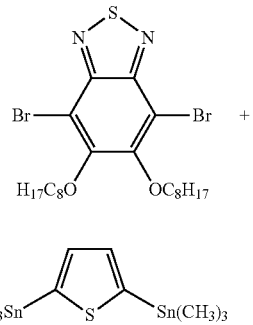

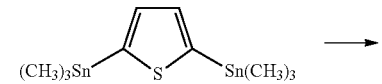

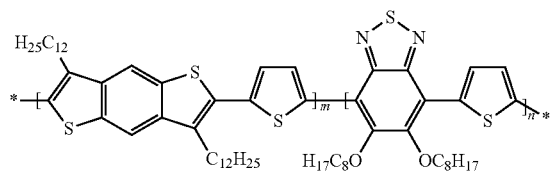

2,6-Dibromo-3,7-didodecyl-benzo[1,2-b;4,5-b']dithiophene (410.8 mg, 0.6000 mmol), 2,5-bis-trimethylstannanyl-thiophene (491.7 mg, 1.200 mmol), 4,7-dibromo-5,6-bis-octyloxy-benzo-2,1,3-thiadiazole (330.2 mg, 0.6000 mmol), P(o-tol)$_3$ (29.2 mg, 0.0800 mmol), Pd$_2$(dba)$_3$ (22.0 mg, 0.0240 mmol) and chlorobenzene (7.5 cm$^3$) were used in the general procedure and the chloroform fraction is precipitated to give a black solid (548 mg, 85%). GPC (140° C., trichlorobenzene): M$_n$=39.6 kg/mol, M$_w$=60.1 kg/mol, PD=1.52.

Poly{[2,6-(2-thienyl)-3,7-di(dodecyl)benzo[1,2-b:4,5-b']dithiophene]-co-4,7-(2-thieno[3,2-b]-thien-5-yl)-5,6-dioctyloxy-2,1,3-benzothiadiazole}(2.2)

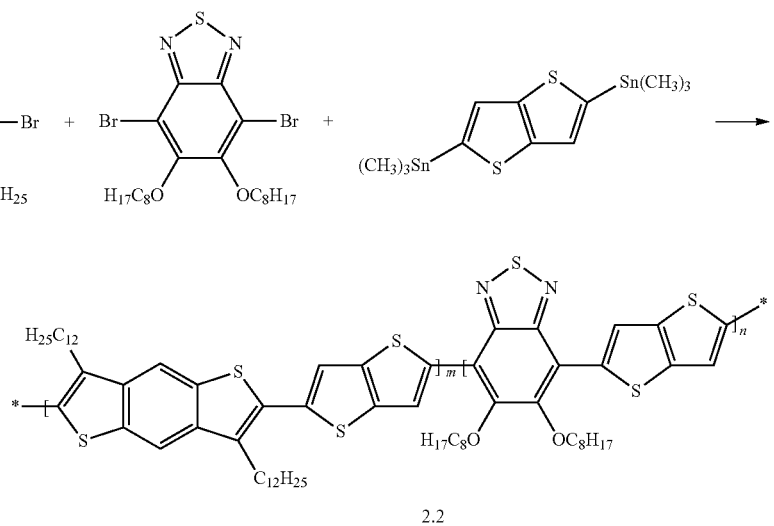

2,6-Dibromo-3,7-didodecyl-benzo[1,2-b;4,5-b']dithiophene (316.0 mg, 0.4620 mmol), 2,5-bis-trimethylstannanyl-thieno[3,2-b]-thiophene (430.0 mg, 0.9230 mmol), 4,7-dibromo-5,6-bis-octyloxy-benzo-2,1,3-thiadiazole (254.0 mg, 0.4620 mmol), P(o-tol)$_3$ (22.5 mg, 0.0740 mmol), Pd$_2$(dba)$_3$ (16.9 mg, 0.0180 mmol) and chlorobenzene (15.0 cm$^3$) were used in the general procedure and the chlorobenzene fraction is precipitated to give a black solid (122 mg, 22%). GPC (140° C., trichlorobenzene): M$_n$=12.7 kg/mol, M$_w$=21.5 kg/mol, PD=1.69.

Poly{[2,6-(2-thienyl)-3,7-di(dodecyl)benzo[1,2-b:4,5-b']dithiophene]-co-4,7-5-(2,2'-bisthien-5'-yl)-5,6-dioctyloxy-2,1,3-benzothiadiazole}(2.3)

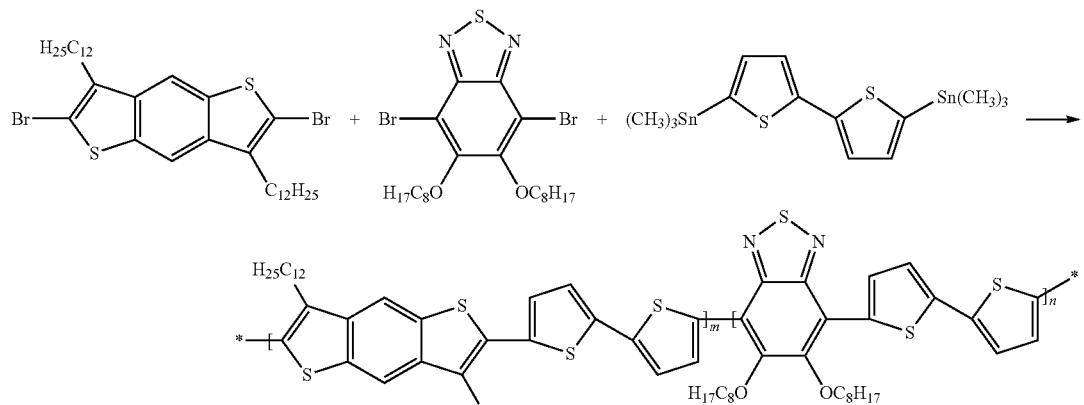

2.3

2,6-Dibromo-3,7-didodecyl-benzo[1,2-b;4,5-b']dithiophene (410.8 mg, 0.6000 mmol), 2,5-bis-trimethylstannanyl-[2,2']-bithiophene (590.3 mg, 1.2000 mmol), 4,7-dibromo-5,6-bis-octyloxy-benzo-2,1,3-thiadiazole (330.2 mg, 0.6000 mmol), P(o-tol)$_3$ (29.2 mg, 0.0960 mmol), Pd$_2$(dba)$_3$ (22.0 mg, 0.0240 mmol) and chlorobenzene (7.5 cm$^3$) were used in the general procedure and the chlorobenzene fraction is precipitated to give a black solid (424 mg, 57%). GPC (140° C., trichlorobenzene): M$_n$=43.3 kg/mol, M$_w$=68.8 kg/mol, PD=1.59.

Poly{[2,6-(2-thienyl)-3,7-di(dodecyl)benzo[1,2-b:4,5-b']dithiophene]-co-4,7-(2-thien-5-yl)-5,6-dioctyloxy-2,1,3-benzo-oxadiazole}(2.4)

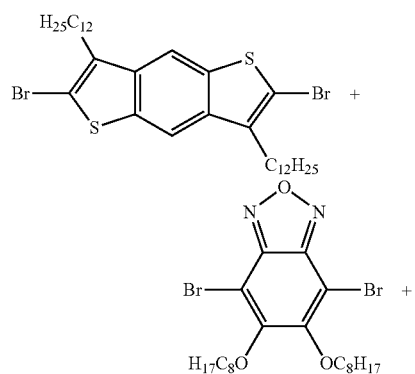

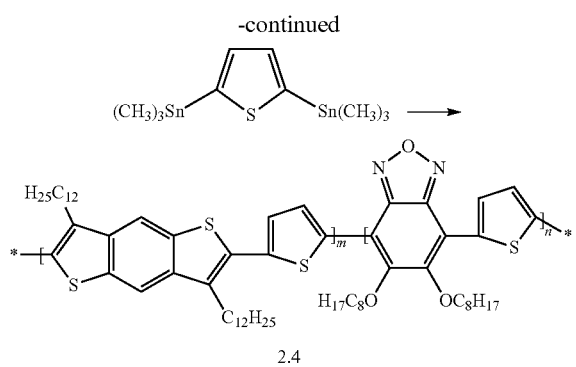

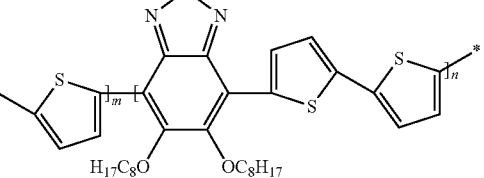

2.4

2,6-Dibromo-3,7-didodecyl-benzo[1,2-b;4,5-b']dithiophene (410.8 mg, 0.6000 mmol), 2,5-bis-trimethylstannanyl-thiophene (491.7 mg, 1.200 mmol), 4,7-dibromo-5,6-bis-octyloxy-benzo-[2,1,3]-oxadiazole (320.6 mg, 0.6000 mmol), P(o-tol)$_3$ (29.2 mg, 0.0800 mmol), Pd$_2$(dba)$_3$ (22.0 mg, 0.0240 mmol) and chlorobenzene (7.5 cm$^3$) were used in the general procedure and the chloroform fraction is precipitated to give a black solid (596 mg, 93%). GPC (140° C., trichlorobenzene): M$_n$=36.7 kg/mol, M$_w$=66.7 kg/mol, PD=1.82.

Example 3

Photovoltaic Cell Fabrication and Measurement

Organic photovoltaic (OPV) devices were fabricated on ITO-glass substrates (13 Ω/sq.) purchased from LUMTEC Corporation. Substrates were cleaned using common solvents (acetone, iso-propanol, deionized-water) in an ultrasonic bath prior to a conventional photolithography process that was carried out to define the bottom electrodes (anodes). A conducting polymer poly(ethylene dioxythiophene) doped with poly(styrene sulfonic acid) [Clevios VPAI 4083 (H. C. Starck)] was mixed in a 1:1 ratio with deionized-water. This solution was sonicated for 20 minutes to ensure proper mixing and filtered using a 0.2 μm filter before spin-coating to achieve a thickness of 20 nm. Substrates were exposed to ozone prior to the spin-coating process to ensure good wetting properties. Films were then annealed at 130° C. for 30 minutes in a nitrogen atmosphere where they were kept for the remainder of the process. Active material solutions (i.e. polymer+PCBM) were prepared and stirred overnight to fully dissolve the solutes. Thin films were either spin-coated or blade-coated in a nitrogen atmosphere to achieve active layer thicknesses between 100 and 200 nm as measured using a profilometer. A short drying period followed to ensure removal of any residual solvent.

Typically, spin-coated films were dried at 23° C. for 10 minutes and blade-coated films were dried at 70° C. for 3 minutes on a hotplate. For the last step of the device fabrication, Ca (30 nm)/Al (200 nm) cathodes were thermally evaporated through a shadow mask to define the cells. Current-voltage characteristics were measured using a Keithley 2400 SMU while the solar cells were illuminated by a Newport Solar Simulator at 100 mW·cm$^{-2}$ white light. The Solar Simulator was equipped with AM1.5G filters. The illumination intensity was calibrated using a Si photodiode. Device preparation and characterization is done in a dry-nitrogen atmosphere.

Power conversion efficiency is calculated using the following expression $$\eta = V_{oc} \times J_{sc} \times FF/P_{in}$$

where FF is defined as $$FF = V_{max} \times J_{max}/V_{oc} \times J_{sc}$$

OPV device characteristics for a 1:1.5 blend of polymer (2): PC$_{61}$BM (coated from a o-dichlorobenzene solution at a total solid concentration of 30 mg·cm$^{-3}$) are shown in Table 1.

TABLE 1

Photovoltaic cell characteristics.

| Blend | η (%) | FF (%) | $V_{oc}$ (mV) | $J_{sc}$ (mA/cm$^2$) |
|---|---|---|---|---|
| Polymer (2.1):PC$_{61}$BM | 3.78 | 53 | 943 | 7.58 |
| Polymer (2.2):PC$_{61}$BM | 1.75 | 44 | 744 | 5.31 |
| Polymer (2.3):PC$_{61}$BM | 2.29 | 67 | 676 | 5.05 |
| Polymer (2.4):PC$_{61}$BM | 3.20 | 69 | 877 | 5.31 |

The invention claimed is:

1. A conjugated polymer consisting of repeating units of formula I1 and repeating units of formula I2

—(Ar$^1$)$_a$—B—      I1

—(Ar$^2$)$_b$-A-      I2 wherein
B is a divalent group of the following formula

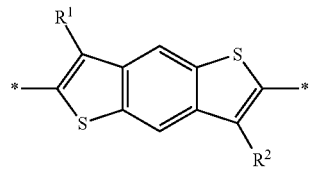

A is a divalent group of the following formula

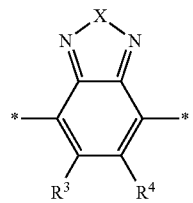

X is O, Se, Te, NR$^0$ or S,
R$^1$, R$^2$ denote independently of each other, and on each occurrence identically or differently, straight-chain, branched or cyclic alkyl with 1 to 30 C atoms,
R$^3$, R$^4$ denote independently of each other, and on each occurrence identically or differently, H, F, or straight-chain or branched alkyl or alkoxy with 1 to 30 C atoms,
Ar$^1$, Ar$^2$ are, on each occurrence identically or differently, and independently of each other, of formula I1, I2, I3, I4, I5 or I6

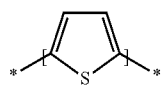
I1

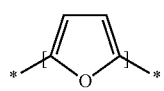
I2

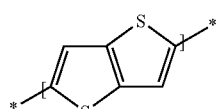
I3

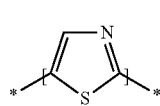
I4

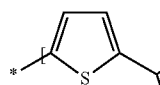
I5

I6 wherein the heterocyclic rings in formulae I1, I2, I3, I4, I5 and I6 are optionally substituted by one or two groups R$^1$ or R$^3$,
R$^S$ is on each occurrence identically or differently F, Br, Cl, —CN, —NC, —NCO, —NCS, —OCN, —SCN, —C(O)NR$^0$R$^{00}$, —C(O)X$^0$, —C(O)R$^0$, —NH$_2$, —NR$^0$R$^{00}$, —SH, —SR$^0$, —SO$_3$H, —SO$_2$R$^0$, —OH, —NO$_2$, —CF$_3$, —SF$_5$, or optionally substituted silyl, carbyl or hydrocarbyl with 1 to 40 C atoms that is optionally substituted and optionally comprises one or more hetero atoms,
R$^0$, R$^{00}$ are independently of each other H or optionally substituted C$_{1-40}$ carbyl or hydrocarbyl,
X$^0$ is halogen, and
a, b are on each occurrence identically or differently 1, 2 or 3.

2. The polymer according to claim 1, which is of formula II:

—([(Ar$^1$)$_a$—B]$_x$—[(Ar$^2$)$_b$-A]$_y$)$_n$-      II wherein
B is a divalent group of the following formula

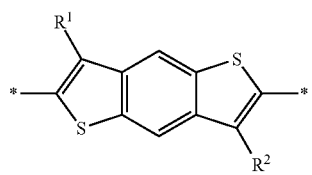

A is a divalent group of the following formula

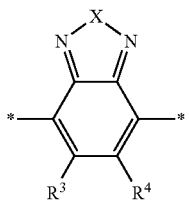

X is O, Se, Te, NR⁰ or S,
R¹, R² denote independently of each other, and on each occurrence identically or differently, straight-chain, branched or cyclic alkyl with 1 to 30 C atoms,
R³, R⁴ denote independently of each other, and on each occurrence identically or differently, H, F, or straight-chain or branched alkyl or alkoxy with 1 to 30 C atoms,
Ar¹, Ar² are, on each occurrence identically or differently, and independently of each other, of formula I1, I2, I3, I4, I5 or I6

I1
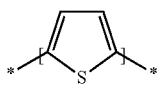

I2
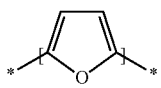

I3
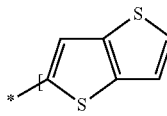

I4
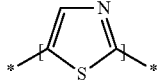

I5
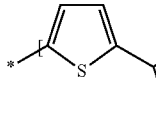

I6
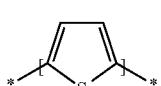

wherein the heterocyclic rings in formulae I1, I2, I3, I4, I5 and I6 are optionally substituted by one or two groups R¹ or R³,
R$^S$ is on each occurrence identically or differently F, Br, Cl, —CN, —NC, —NCO, —NCS, —OCN, —SCN, —C(O)NR⁰R⁰⁰, —C(O)X⁰, —C(O)R⁰, —NH₂, —NR⁰R⁰⁰, —SH, —SR⁰, —SO₃H, —SO₂R⁰, —OH, —NO₂, —CF₃, —SF₅, or optionally substituted silyl, carbyl or hydrocarbyl with 1 to 40 C atoms that is optionally substituted and optionally comprises one or more hetero atoms,
R⁰, R⁰⁰ are independently of each other H or optionally substituted C₁₋₄₀ carbyl or hydrocarbyl,
X⁰ is halogen,
a, b are on each occurrence identically or differently 1, 2 or 3,
x is the mole fraction of units (Ar¹)$_a$-B and is >0 and <1,
y is the mole fraction of units (Ar²)$_b$-A and is >0 and <1,
x+y is 1, and
n is an integer >1.

3. The polymer according to claim 1, which is of formula II1 or II2

*—[Ar¹—B—Ar²-A]$_n$-*    II1

*—[(Ar¹—B)$_x$—(Ar²-A)$_y$]$_n$-*    II2 wherein
B is a divalent group of the following formula

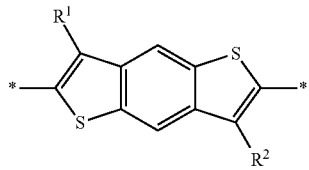

A is a divalent group of the following formula

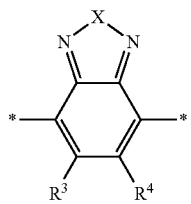

X is O, Se, Te, NR⁰ or S,
R¹, R² denote independently of each other, and on each occurrence identically or differently, straight-chain, branched or cyclic alkyl with 1 to 30 C atoms,
R³, R⁴ denote independently of each other, and on each occurrence identically or differently, H, F, or straight-chain or branched alkyl or alkoxy with 1 to 30 C atoms,
Ar¹, Ar² are, on each occurrence identically or differently, and independently of each other, of formula I1, I2, I3, I4, I5 or I6

I1
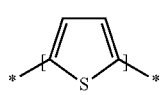

I2
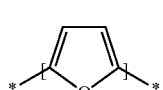

I3
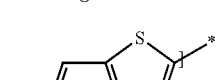

I4
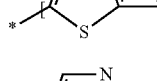

I5
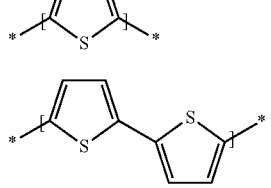

I6
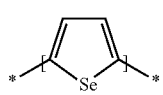

wherein the heterocyclic rings in formulae I1, I2, I3, I4, I5 and I6 are optionally substituted by one or two groups R¹ or R³,
R$^S$ is on each occurrence identically or differently F, Br, Cl, —CN, —NC, —NCO, —NCS, —OCN, —SCN, —C(O)NR⁰R⁰⁰, —C(O)X⁰, —C(O)R⁰, —NH₂, —NR⁰R⁰⁰, —SH, —SR⁰, —SO₃H, —SO₂R⁰, —OH, —NO₂, —CF₃, —SF₅, or optionally substituted silyl, carbyl or hydrocarbyl with 1 to 40 C atoms that is optionally substituted and optionally comprises one or more hetero atoms, R⁰, R⁰⁰ are independently of each other H or optionally substituted $C_{1-40}$ carbyl or hydrocarbyl, X⁰ is halogen, a, b are on each occurrence identically or differently 1, 2 or 3, x is the mole fraction of units $(Ar^1)_a$-B and is >0 and <1, y is the mole fraction of units $(Ar^2)_b$-A and is >0 and <1, x+y is 1, and n is an integer >1.

4. The polymer according to claim 1, which is of formula III $$R^5\text{-chain-}R^6 \qquad \qquad \text{III}$$

wherein chain is a polymer chain of formula II, II1 or II2

$$-([(Ar^1)_a-B]_x-[(Ar^2)_b-A]_y)_n-, \qquad \text{II}$$

$$*-[Ar^1-B-Ar^2-A]_n-* \qquad \text{II1}$$

$$*-[(Ar^1-B)_x-(Ar^2-A)_y]_n-* \qquad \text{II2}$$

B is a divalent group of the following formula

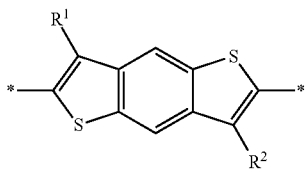

A is a divalent group of the following formula

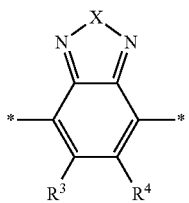

X is O, Se, Te, NR⁰ or S,

R¹, R² denote independently of each other, and on each occurrence identically or differently, straight-chain, branched or cyclic alkyl with 1 to 30 C atoms, R³, R⁴ denote independently of each other, and on each occurrence identically or differently, H, F, or straight-chain or branched alkyl or alkoxy with 1 to 30 C atoms, Ar¹, Ar² are, on each occurrence identically or differently, and independently of each other, of formula I1, I2, I3, I4, I5 or I6

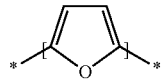
I1

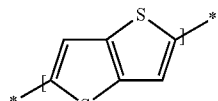
I2

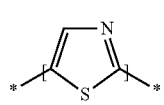
I3

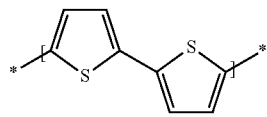
I4

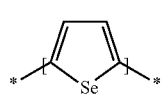
I5

I6 wherein the heterocyclic rings in formulae I1, I2, I3, I4, I5 and I6 are optionally substituted by one or two groups R¹ or R³, $R^S$ is on each occurrence identically or differently F, Br, Cl, —CN, —NC, —NCO, —NCS, —OCN, —SCN, —C(O)NR⁰R⁰⁰, —C(O)X⁰, —C(O)R⁰, —NH₂, —NR⁰R⁰⁰, —SH, —SR⁰, —SO₃H, —SO₂R⁰, —OH, —NO₂, —CF₃, —SF₅, or optionally substituted silyl, carbyl or hydrocarbyl with 1 to 40 C atoms that is optionally substituted and optionally comprises one or more hetero atoms, R⁰, R⁰⁰ are independently of each other H or optionally substituted $C_{1-40}$ carbyl or hydrocarbyl, X⁰ is halogen, a, b are on each occurrence identically or differently 1, 2 or 3, x is the mole fraction of units $(Ar^1)_a$-B and is >0 and <1, y is the mole fraction of units $(Ar^2)_b$-A and is >0 and <1, x+y is 1, n is an integer >1, R⁵ and R⁶ denote independently of each other H, F, Br, Cl, —CH₂Cl, —CHO, —CH=CH₂, —SiR'R''R''', —Sn-R'R''R''', —BR'R'', —B(OR')(OR''), —B(OH)₂, —C≡CH, —C≡CSiR'₃, —ZnX⁰ or an endcap group, X⁰ is halogen, and R', R'' and R''' are independently of each other H or optionally substituted $C_{1-40}$ carbyl or hydrocarbyl, or two of R', R'' and R''' optionally form a ring together with the hetero atom to which they are attached.

5. The polymer according to claim 1, wherein Ar¹ and Ar² are of the following formulae

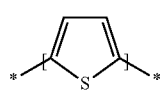
I1

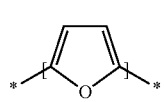
I2

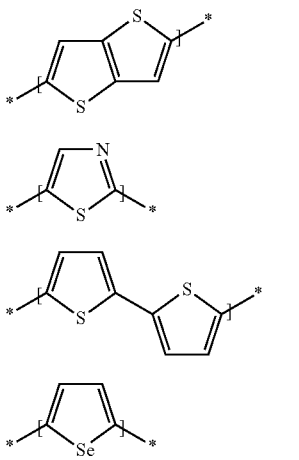

wherein the heterocyclic rings are optionally substituted by one or two groups $R^1$ or $R^3$, $R^1$ denotes on each occurrence identically or differently, straight-chain, branched or cyclic alkyl with 1 to 30 C atoms, $R^3$ denotes on each occurrence identically or differently, H, F, or straight-chain or branched alkyl or alkoxy with 1 to 30 C atoms.

6. The polymer according to claim 1, wherein $R^S$ is on each occurrence identically or differently F, Br, Cl, —CN, —NC, —NCO, —NCS, —OCN, —SCN, —C(O)NR°R°°, —C(O)X°, —C(O)R°, —NH$_2$, —NR°R°°, —SH, —SR°, —SO$_3$H, —SO$_2$R°, —OH, —NO$_2$, —CF$_3$, —SF$_5$, or silyl, carbyl or hydrocarbyl with 1 to 40 C atoms and optionally comprises one or more hetero atoms.

7. A mixture or blend comprising one or more polymers according to claim 1 and one or more additional compounds or polymers having semiconducting, charge transport, hole/electron transport, hole/electron blocking, electrically conducting, photoconducting or light emitting properties.

8. The mixture or blend according to claim 7, which comprises one or more n-type organic semiconductor compounds.

9. The mixture or blend according to claim 8, wherein the n-type organic semiconductor compound is a fullerene or substituted fullerene.

10. A formulation comprising
one or more solvents, and
one or more polymers according to claim 1, or
a mixture or blend comprising said one or more polymers and one or more additional compounds or polymers having semiconducting, charge transport, hole/electron transport, hole/electron blocking, electrically conducting, photoconducting or light emitting properties.

11. A charge transport, semiconducting, electrically conducting, photoconducting or light emitting material in an optical, electrooptical, electronic, electroluminescent or photoluminescent component or device, comprising
one or more polymers according to claim 1 or
a mixture or blend comprising said one or more polymers and one or more additional compounds or polymers having semiconducting, charge transport, hole/electron transport, hole/electron blocking, electrically conducting, photoconducting or light emitting properties, or
a formulation comprising one or more solvents, and said one or more polymers, mixture or blend.

12. An optical, electrooptical or electronic component or device comprising
one or more polymers according to claim 1 or
a mixture or blend comprising said one or more polymers and one or more additional compounds or polymers having semiconducting, charge transport, hole/electron transport, hole/electron blocking, electrically conducting, photoconducting or light emitting properties, or
a formulation comprising one or more solvents, and said one or more polymers, mixture or blend.

13. The component or device according to claim 12, which is selected from the group consisting of organic field effect transistors (OFET), thin film transistors (TFT), integrated circuits (IC), logic circuits, capacitors, radio frequency identification (RFID) tags, organic light emitting diodes (OLED), organic light emitting transistors (OLET), flat panel displays, backlights of displays, organic photovoltaic devices (OPV), organic solar cells (O-SC), organic photodetector (OPD), photodiodes, laser diodes, photoconductors, photodetectors, electrophotographic devices, electrophotographic recording devices, organic memory devices, sensor devices, charge injection layers, charge transport layers in polymer light emitting diodes (PLEDs), interlayers in polymer light emitting diodes (PLEDs), Schottky diodes, planarising layers, antistatic films, polymer electrolyte membranes (PEM), conducting substrates, conducting patterns, electrode materials in batteries, alignment layers, biosensors, biochips, security markings, security devices, and components or devices for detecting and discriminating DNA sequences.

14. The component or device according to claim 12, which is an OFET, bulk heterojunction (BHJ) OPV device or inverted BHJ OPV device.

15. A process for preparing a polymer according to claim 1, comprising coupling one or more of the following monomers $$R^5—(Ar^1)_c—B—(Ar^2)_d—R^6 \qquad \text{IV}$$

$$R^5—Ar^1—B—Ar^2—R^6 \qquad \text{IV1}$$

$$R^5—B—R^6 \qquad \text{IV2}$$

$$R^5—Ar^1—B—R^6 \qquad \text{IV3}$$

$$R^5—B—Ar^2—R^6 \qquad \text{IV4}$$

wherein
B is a divalent group of the following formula

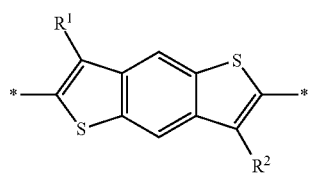

$R^1$, $R^2$ denote independently of each other, and on each occurrence identically or differently, straight-chain, branched or cyclic alkyl with 1 to 30 C atoms, $Ar^1$, $Ar^2$ are, on each occurrence identically or differently, and independently of each other, of formula I1, I2, I3, I4, I5 or I6

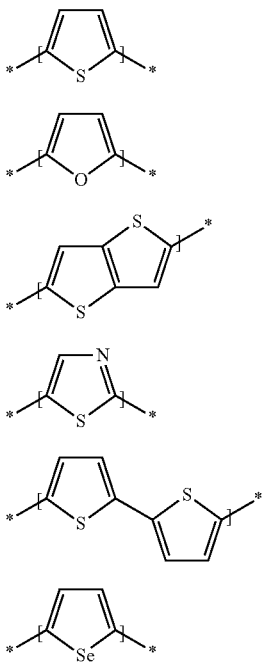

wherein the heterocyclic rings in formulae I1, I2, I3, I4, I5 and I6 are optionally substituted by one or two groups $R^1$ or $R^3$, $R^S$ is on each occurrence identically or differently F, Br, Cl, —CN, —NC, —NCO, —NCS, —OCN, —SCN, —C(O)NR°R°°, —C(O)X°, —C(O)R°, —NH$_2$, —NR°R°°, —SH, —SR°, —SO$_3$H, —SO$_2$R°, —OH, —NO$_2$, —CF$_3$, —SF$_5$, or optionally substituted silyl, carbyl or hydrocarbyl with 1 to 40 C atoms that is optionally substituted and optionally comprises one or more hetero atoms, R°, R°° are independently of each other H or optionally substituted C$_{1-40}$ carbyl or hydrocarbyl, c and d are independently of each other 0, 1, 2 or 3, $R^5$ and $R^6$ denote independently of each other Cl, Br, I, O-tosylate, O-triflate, O-mesylate, O-nonaflate, —SiMe$_2$F, —SiMeF$_2$, —O—SO$_2$Z$^1$, —B(OZ$^2$)$_2$, —CZ$^3$=C(Z$^3$)$_2$, —C≡CH, —C≡CSi(Z$^1$)$_3$, —ZnX° or —Sn(Z$^4$)$_3$, X° is halogen, and Z$^{1-4}$ are selected from the group consisting of alkyl and aryl, each being optionally substituted, and two groups Z$^2$ optionally form a cyclic group, with one or more monomers of formula C, and optionally with one or more monomers of formula D and/or E, in an aryl-aryl coupling reaction $R^5$—(Ar$^2$)$_d$-A-(Ar$^1$)$_c$—R$^6$        C $R^5$—(Ar$^1$)$_a$—R$^6$        D $R^5$—(Ar$^2$)$_b$—R$^6$        E wherein A is a divalent group of the following formula

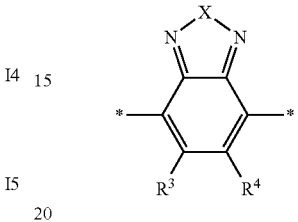

X is O, Se, Te, NR° or S, $R^3$, $R^4$ denote independently of each other, and on each occurrence identically or differently, H, F, or straight-chain or branched alkyl or alkoxy with 1 to 30 C atoms, and a, b are on each occurrence identically or differently 1, 2 or 3.

16. The process according to claim 15, wherein a monomer of formula VI is coupled.

17. The process according to claim 15, wherein a monomer of formula IV1, IV2, IV3 or IV4 is coupled.

18. The polymer according to claim 2,
wherein $R^S$ is on each occurrence identically or differently F, Br, Cl, —CN, —NC, —NCO, —NCS, —OCN, —SCN, —C(O)NR°R°°, —C(O)X°, —C(O)R°, —NH$_2$, —NR°R°°, —SH, —SR°, —SO$_3$H, —SO$_2$R°, —OH, —NO$_2$, —CF$_3$, —SF$_5$, or silyl, carbyl or hydrocarbyl with 1 to 40 C atoms and optionally comprises one or more hetero atoms.

19. The monomer according to claim 16,
wherein $R^S$ is on each occurrence identically or differently F, Br, Cl, —CN, —NC, —NCO, —NCS, —OCN, —SCN, —C(O)NR°R°°, —C(O)X°, —C(O)R°, —NH$_2$, —NR°R°°, —SH, —SR°, —SO$_3$H, —SO$_2$R°, —OH, —NO$_2$, —CF$_3$, —SF$_5$, or silyl, carbyl or hydrocarbyl with 1 to 40 C atoms and optionally comprises one or more hetero atoms.

* * * * *